(12) United States Patent
Amedio, Jr. et al.

(10) Patent No.: US 8,604,007 B2
(45) Date of Patent: Dec. 10, 2013

(54) SALTS OF ISOPHOSPHORAMIDE MUSTARD AND ANALOGS THEREOF

(75) Inventors: John C. Amedio, Jr., Franklin, MA (US); Barbara P. Wallner, Cohasset, MA (US); Philip B. Komarnitsky, Chestnut Hill, MA (US)

(73) Assignee: Ziopharm Oncology, Inc., Charlestown, MA (US)

( * ) Notice: Subject to any disclaimer, the term of this patent is extended or adjusted under 35 U.S.C. 154(b) by 1357 days.

(21) Appl. No.: 12/080,812

(22) Filed: Apr. 4, 2008

(65) Prior Publication Data

US 2008/0255056 A1 Oct. 16, 2008

Related U.S. Application Data

(60) Provisional application No. 60/922,148, filed on Apr. 6, 2007, provisional application No. 60/927,363, filed on May 2, 2007, provisional application No. 60/934,914, filed on Jun. 15, 2007, provisional application No. 61/001,237, filed on Oct. 30, 2007.

(51) Int. Cl.
*A61K 31/675* (2006.01)
(52) U.S. Cl.
USPC .............. 514/89; 514/76; 514/740; 558/199; 564/12
(58) Field of Classification Search
None
See application file for complete search history.

(56) References Cited

U.S. PATENT DOCUMENTS

| 5,055,459 | A | 10/1991 | Andersson et al. |
| 5,091,552 | A | 2/1992 | Farquhar |
| 5,468,499 | A | 11/1995 | Chan et al. |
| 2008/0255056 | A1 | 10/2008 | Amedio et al. |

FOREIGN PATENT DOCUMENTS

| JP | 51-059886 | | 5/1976 |
| SU | 427945 | A1 | 5/1974 |
| WO | WO-00/71134 | | 11/2000 |
| WO | WO-01/79158 | A2 | 10/2001 |
| WO | WO 2006/047575 | | 5/2006 |

OTHER PUBLICATIONS

Han et al., "Synthesis of $^{17}$O (and $^{18}$O) Labelled Isophosphoramide Mustard" Journal of Labelled Compounds and Radiopharmaceuticals 34(3):247-254 (1994).
Misiura et al., Isophosphoramide mustard analogues as prodrugs for anti-cancer gene-directed enzyme-prodrug therapy (GDEPT) Acta Biochimica Polonica 49(1):169-176 (2002).
Pohl et al., "D-19575—A Sugar-Linked Isophosphoramide Mustard Derivative Exploiting Transmembrane Glucose Transport", Cancer Chemotherapy and Pharmacology, vol. 35(5):364-370 (1994).
Wagner, "Intrasubject Variation in Elimination Half-lives of Drugs Which Are Appreciably Metabolized", Journal of Pharmacokinetics and Biopharmaceutics, 1(2):165-173 (1973).
Zakharov et al., "Catalytic Phosphorylation of Polyfluoroalkanols. 5. Catalytic Phosphorylation of α-polyfluoroalkylbenzyl Alcohols with Phosphoryl Chloride", Bulletin of the Academy of Sciences of the USSR 25(8):1727-31 (1976).
Database Beilstein [online], Beilstein Institute for Organic Chemistry, Frankfurt-Main, DE, XP002368999, Database accession No. BRN 2249643, abstract, and Breil, S. et al.: Phosphorus, Sulfur Silicon Relat. Elem., 177(8-9):1939-1940 (2002).
Database Beilstein [online], Beilstein Institute for Organic Chemistry, Frankfurt-Main, DE, XP002453066, Database accession No. BRN 6845680, abstract, Shulman-Roskes et al.: J. Labelled Compd. Radiopharm., 34(3):231-238 (1994).
Database Beilstein [online], Beilstein Institute for Organic Chemistry, Frankfurt-Main, DE, XP002453070 retrieved from XFIRE, Database accession No. 9763485, abstract, Misiura, K.: Pharmazie, 59(9):668-672 (2004).
Database Beilstein [online], Beilstein Institute for Organic Chemistry, Frankfurt-Main, DE, XP002453071 retrieved from XFIRE, Database accession No. BRN 9261194, BRN 9259456, abstract, Rouveze et al.: Phosphorus, Sulfur, Silicon Relat. Elem., 177(6-7):1735-1738 (2002).
Database Beilstein [online], Beilstein Institute for Organic Chemistry, Frankfurt-Main, DE, XP002453072 retrieved from XFIRE, Database accession No. BRN 8468593, BRN 8458718, abstract, Dirven et al.: Chem. Res. Toxicol., 8(7):979-986 (1995).
Database Beilstein [online], Beilstein Institute for Organic Chemistry, Frankfurt-Main, DE; XP002369000, Database accession No. BRN 6835849 abstract, and Shulman-Roskes et al.: J. Labelled Compd. Radiopharm., 34(3):231-238 (1994).
Database BIOSIS [online], Biosciences Information Service, Philadelphia, PA, US (1994), Shulman-Roskes Ellen M. et al., "Synthesis of 15N labeled isophosphoramide mustard," XP002369092, Database accession No. PREV199497274456 abstract and Journal of Labelled Compounds and Radiopharmaceuticals, 34(3)231-237 (1994).
Database CA [online] Chemical Abstracts Service, Columbus, OH, US; Millis et al., "Comparison of the Protonation of Isophosphoramide Mustard and Phosphoramide Mustard," XP002453068, retrieved from STN Database accession No. 1995:592274, abstract.
Boal et al., "$^{31}$P NMR Studies of the Kinetics of Bisalkylation by Isophosphoramide Mustard: Comparisons with Phosphoramide Mustard," J. Med. Chem., 32(8):1768-1773 (1989).
Cole et al., "Gas chromatography-electron ionization mass spectrometry and liquid chromatography-electrospray tandem mass spectrometry for determination of impurities in the anti-cancer drug isophosphoramide mustard," International Journal of Mass Spectrometry, 231:147-155 (2004).

(Continued)

*Primary Examiner* — Sudhakar Katakam
(74) *Attorney, Agent, or Firm* — Wilmer Cutler Pickering Hale and Dorr LLP

(57) ABSTRACT

Disclosed herein are crystalline compounds of formula (I) wherein A$^+$ represents a hydroxylated aliphatic ammonium species; and X and Y independently represent leaving groups.

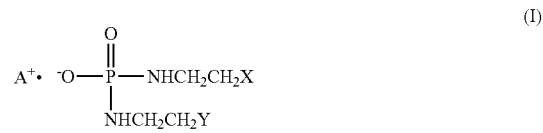

(I)

29 Claims, 33 Drawing Sheets

(56) References Cited

OTHER PUBLICATIONS

Germann et al., "Comparative preclinical toxicology and pharmacology of isophosphoramide mustard, the active metabolite of ifosfamide," Cancer Chemotherapy and Pharmacology, Springer-Verlag Heidelberg, 55:143-151 (2005). Epub 2004.

Ludeman et al., "Synthesis and Antitumor Activity of Cyclophosphamide Analogues. 4. Preparation, Kinetic Studies, and Anticancer Screening of 'Phenylketophosphamide' and Similar Compounds Related to the Cyclophosphamide Metabolite Aldophosphamide," J. Med. Chem., 29(5):716-727 (1986).

Millis et al., "Comparison of the Protonation of Isophosphoramide Mustard and Phosphoramide Mustard," J. Med. Chem., 38(12):2166-2175 (1995).

Rauen et al., "Alkylans-Alkylandum-Reaktionen 2-Chloräthylamin Und Phosphamidverbindungen Als Alkylantien," Arzneimittel Forschung. Drug Research, ECV Editio Cantor Verlag, Aulendorf, DE, 21(4):518-524 (1971) XP001105865.

Springer et al., "Isophosphoramide Mustard and Its Mechanism of Bisalkylation," J. Org. Chem., 63(21):7218-7222 (1998).

Struck et al., "Isophosphoramide mustard, a metabolite of ifosfamide with activity against murine tumours comparable to cyclophosphamide," Br. J. Cancer, 47:015-026 (1983).

Voelcker, G., et al., "Structure/activity studies with thiazolidinyl- and perhydrothiazinyl-phosphamide esters," Journal of Cancer Research and Clinical Oncology, vol. 124(6):297-300 (1998).

Zheng et al., "Preclinical pharmacokinetics and stability of isophosphoramide mustard," Cancer Chemother Pharmacol, 33:391-398 (1994).

European Search Report dated Sep. 28, 2007 for EP 05821125.

International Search Report dated Jun. 23, 2006 for PCT/US2005/038523.

Parial International Search Report dated Jun. 11, 2008 for PCT/US2008/004449.

SALTS OF ISOPHOSPHORAMIDE MUSTARD AND ANALOGS THEREOF

CROSS REFERENCE TO RELATED APPLICATIONS

This application claims the benefit of U.S. Provisional Patent Application Ser. No. 60/922,148 filed on Apr. 6, 2007, U.S. Provisional Patent Application Ser. No. 60/927,363 filed on May 2, 2007, U.S. Provisional Patent Application Ser. No. 60/934,914 filed on Jun. 15, 2007 and U.S. Provisional Patent Application Ser. No. 61/001,237 filed on Oct. 30, 2007. The teachings of all of the referenced applications are incorporated by reference in their entirety.

BACKGROUND OF THE INVENTION

Autopsies of soldiers killed by mustard gas in World War I indicated that sulfur mustard has a disproportionate effect on rapidly dividing cells and suggested that sulfur mustard compounds might have antitumor effects. Indeed, early researchers attempted to treat cancer by direct injection of sulfur mustard into tumors. This research was limited by the extreme toxicity of sulfur mustard compounds and nitrogen mustard analogs, such as mechlorethamine, were investigated as less toxic alternatives.

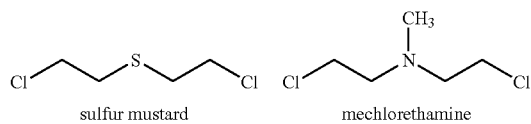

sulfur mustard    mechlorethamine

Because of the lack of selectivity of most mechlorethamine analogs, prodrugs, such as phosphoramide compounds, which can be activated by the high concentration of phosphoramidases present in neoplastic cells, have been investigated. Two phosphoramide alkylating agents, cyclophosphamide (CPA) and the isomeric compound Ifosfamide (Ifos) have proved to be particularly effective.

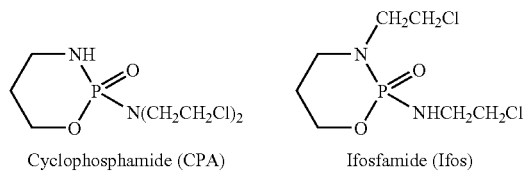

Cyclophosphamide (CPA)    Ifosfamide (Ifos)

With reference to FIG. 1, isophosphoramide mustard (IPM) is a common metabolite of CPA and Ifos. IPM is thought to be responsible for at least a portion of the antitumor activity exhibited by CPA and Ifos. Efforts to use IPM as an anticancer agent directly have been unsuccessful due in part to the compound's instability. IPM has been synthesized and preliminary biological evaluations of the compound have been conducted, but unfortunately IPM is too unstable to be isolated and used for human treatment.

SUMMARY OF THE INVENTION

Disclosed herein are crystalline compounds of formula (I)

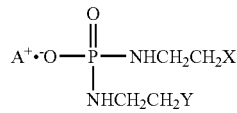

wherein $A^+$ represents an aliphatic ammonium species; and X and Y independently represent leaving groups.

In certain embodiments, the invention relates to pharmaceutical compositions, comprising a compound of formula (I) and a pharmaceutically acceptable diluent or carrier. Methods of preparing such compounds and compositions are also described.

Also disclosed herein are a lyophilisate and a method for producing a lyophilisate comprising isophosphoramide mustard (IPM) and/or an IPM analog, one or more equivalents of a base, and an excipient. In certain embodiments, the method comprises contacting a crystalline salt of IPM or an analog thereof and an aliphatic amine, such as tris(hydroxymethyl)aminomethane (Tris), or a mixture of IPM or an analog thereof and one or more aliphatic amines (preferably in a ratio of about 1:1 of IPM or analog thereof to the amine or amines) with water and lyophilizing the resulting mixture. In certain embodiments, the mixture and the resulting lyophilisate comprise an excipient, such as mannitol, anhydrous lactose, sucrose, D(+)-trehalose, dextran 40 or povidone (PVP K24), preferably mannitol.

Such formulations include lyophilisates, preferably comprising an excipient, such as mannitol, anhydrous lactose, sucrose, D(+)-trehalose, dextran 40 or povidone (PVP K24), preferably mannitol, and a compound of the formula

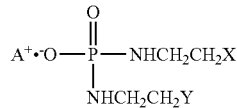

wherein $A^+$ represents an ammonium species selected from the protonated (conjugate acid) or quaternary forms of aliphatic amines and aromatic amines, including basic amino acids, heterocyclic amines, substituted and unsubstituted pyridines, guanidines and amidines; and X and Y independently represent leaving groups.

Also disclosed herein are pharmaceutical compositions adapted for oral administration, comprising a pharmaceutically acceptable diluent or excipient and a compound as disclosed herein.

In certain embodiments, the invention relates to methods for the treatment of hyperproliferative disorders, e.g., with the compounds or formulations discussed herein. In certain such embodiments, the invention relates to the treatment of a hyperproliferative disorder selected from leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Additional examples of conditions that may be treated using the disclosed compounds and compositions include solid tumors, such as sarcomas and carcinomas, including, but not limited to fibrosarcoma, myxosarcoma, liposarcoma, chondrosarcoma, osteogenic sarcoma, cyclophosphamide-resistant sarcomas, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, bladder carcinoma, and CNS tumors (such as a glioma, astrocytoma, medulloblastoma, craniopharyogioma, ependymoma, pinealoma, hemangioblastoma, acoustic neuroma, oligodendroglioma, menangioma, melanoma, neuroblastoma and retinoblastoma).

DETAILED DESCRIPTION OF THE INVENTION

I. IPM SALTS AND ANALOGS THEREOF

Figure 1:
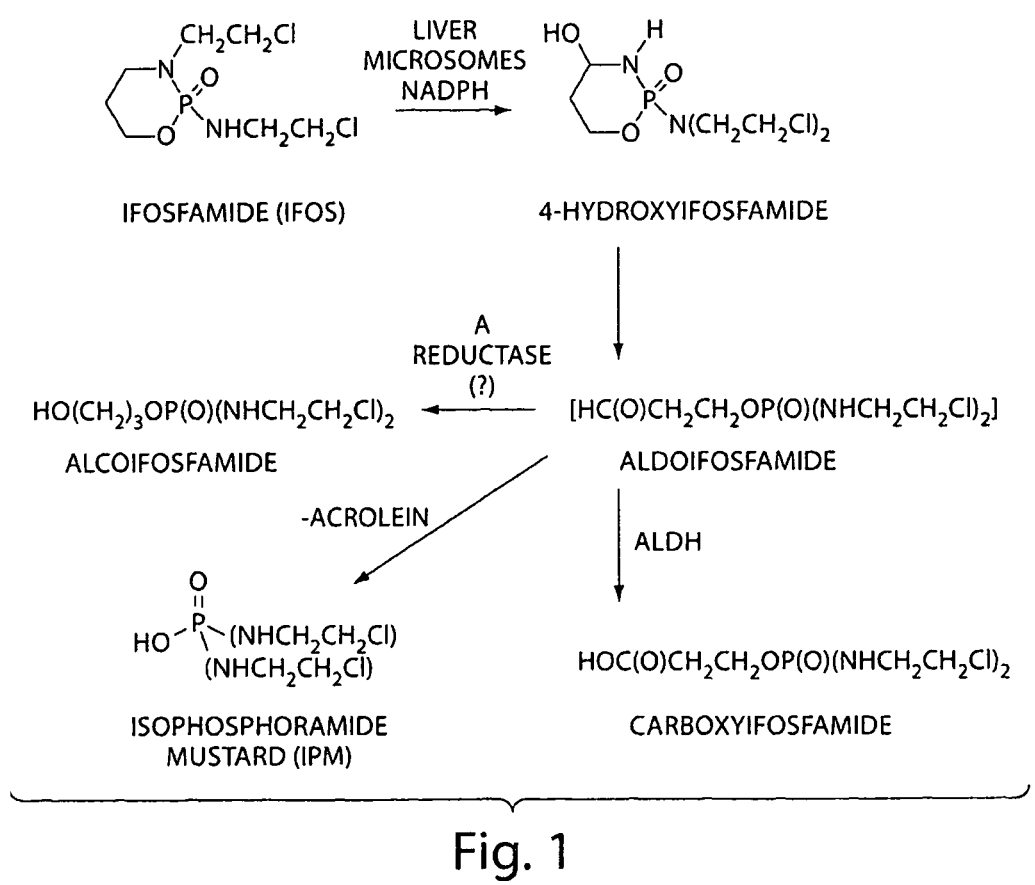
FIG. 1 is a scheme illustrating the metabolism of ifosfamide including the production of acrolein and isophosphoramide mustard.

The compositions disclosed herein include crystalline IPM salts or analogs thereof. In certain embodiments, the disclosed salts include one or more cations. In certain embodiments, the cations can be a conjugate acid of an amine base or can be a quaternary ammonium cation.

In certain embodiments, the disclosed crystalline compounds comprise salts of IPM or an analog thereof. Such compounds include crystalline compounds of formula (I)

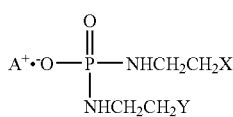

(I)

wherein A$^+$ represents an ammonium species selected from the protonated (conjugate acid) or quaternary forms of hydroxylated aliphatic amines; and X and Y independently represent leaving groups. In certain embodiments, X and Y are independently halogen. Preferably X and Y are the same. In certain such embodiments, X and Y are both Cl.

Particular examples of suitable conjugate acids of amine bases include, without limitation, the conjugate acid of mono-, bis- or tris-(2-hydroxyethyl)amine, 2-hydroxy-tert-butylamine, N,N-dimethyl-N-(2-hydroxyethyl)amine, and tris(hydroxymethyl)aminomethane (Tris). In certain such embodiments, A$^+$ is the conjugate acid of Tris.

In certain embodiments, the invention relates to a compound comprising a crystalline salt of IPM or analog thereof wherein the IPM or analog thereof, and the counterion, preferably Tris, are present in a ratio from 2:1 to 1:2, preferably 1:1. In certain embodiments, the crystalline composition comprises more than one polymorphic form of crystals, such as two, three, four, or even five polymorphic forms of crystals. In certain alternative such embodiments, the crystalline composition comprises a single polymorphic form of crystals. In certain embodiments, such salts are more stable than IPM and IPM analogs as free acids.

In certain such embodiments, the compound is a crystalline salt of a 1:1 ratio of IPM and Tris. In certain such embodiments, the melting point of the crystalline solid is between about 100 and about 110° C., about 102 to about 108° C., about 103 to about 106° C., or even 105 to 106° C.

In certain embodiments, the compound, e.g., a crystalline salt of a 1:1 ratio of IPM and Tris, is at least about 80% pure, at least about 85% pure, at least 90% pure, at least 95% pure, at least 97% pure, at least 98% pure, or even at least 99% pure. In certain such embodiments, no single impurity exceeds 1% by weight. In certain embodiments, purity is measured relative to all other components of the composition, while in other embodiments (e.g., where the compound is part of a pharmaceutical composition or lyophilisate mixture), purity may be measured relative to degradation products of the compound (e.g., phosphorous-containing degradation products of the compound) or by-products of the manufacture of the compound (e.g., phosphorous-containing degradation products of the compound), thereby excluding other components purposefully added to the composition.

In certain embodiments, the compounds are IPM salts or analogs thereof, wherein the salt has a half-life at room temperature (e.g., about 23° C.) in the presence of water that is greater than a half-life of IPM (i.e., as the free acid) in the presence of water under the same conditions. In certain such embodiments, an IPM salt has a half-life in the presence of water that is equal to or greater than twice as long as IPM itself in the presence of water, more preferably, equal to or greater than five times.

In certain embodiments, the compounds are IPM salts and analogs thereof, wherein the salts are stable at room temperature in the presence of water for at least one day, two days, three days, four days, five days, six days, or even a week.

As used herein, the term "stable" means that the purity of the IPM salt or analog thereof after a period of time (e.g., one month, two months, three months, six months, one year, etc.) is at least 90%, at least 95%, at least 97%, or even at least 99% of the initial purity, which may be determined e.g., by HPLC using evaporative light scattering detection (ELSD). Such an assay may be performed, for example, using a C18 column and an isocratic system with a mobile phase comprising 0.005 M heptafluorobutyric acid and 0.1% trifluoroacetic acid in water.

In certain embodiments, the invention relates to lyophilisates comprising a compound of the formula

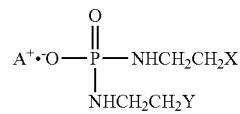

wherein A$^+$ represents an ammonium species selected from the protonated (conjugate acid) or quaternary forms of aliphatic amines and aromatic amines, including basic amino acids, heterocyclic amines, substituted and unsubstituted pyridines, guanidines and amidines; and X and Y independently represent leaving groups.

Particular examples of suitable amine bases (and their corresponding ammonium ions) for use in the present compounds include, without limitation, pyridine, N,N-dimethylaminopyridine, diazabicyclononane, diazabicycloundecene, N-methyl-N-ethylamine, diethylamine, triethylamine, diisopropylethylamine, mono-, bis- or tris-(2-hydroxyethyl)amine, 2-hydroxy-tert-butylamine,tris(hydroxymethyl)aminomethane, N,N-dimethyl-N-(2-hydroxyethyl)amine, tri-(2-hydroxyethyl)amine and N-methyl-D-glucamine.

In certain embodiments, the invention relates to lyophilisates comprising compound of the formula

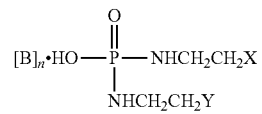

With reference to the formula, B can be, for each n, an independently selected basic molecule. In one embodiment of the formula, B can be selected from the basic amino acids, acyclic aliphatic amines, di- and tri alkyl amines, heterocyclic aliphatic amines, aromatic amines, substituted and unsubstituted pyridines, cyclic and acyclic guanidines, and cyclic and acyclic amidines. Typically, n is from 1 to about 3 such that the formula can include different basic molecules. With continued reference to the formula, X and Y are leaving groups. A person of ordinary skill in the art will understand that the illustrated isophosphoramide mustard structure includes an acidic proton, and as such exists predominantly as its conjugate base at physiological pH and in the presence of a base such as B. Likewise, B, being a basic group exists predominantly as its conjugate acid at physiological pH and in the presence of isophosphoramide mustard and isophosphoramide mustard analogs. Exemplary embodiments of the disclosed compounds are depicted in Table 1.

TABLE 1

$$[B]_n \cdot HO-\overset{O}{\underset{NHCH_2CH_2Y}{\overset{\|}{P}}}-NHCH_2CH_2X$$

| B | n | X | Y |
|---|---|---|---|
| lysine | 2 | Cl | Cl |
| NH$_3$ | 2 | Cl | Cl |
| cyclohexylamine | 2 | Cl | Cl |
| N-methyl-D-glucamine | 2 | Cl | Cl |
| N,N-dimethylaminopyridine | 1 | Cl | Cl |
| arginine | 2 | Cl | Cl |
| lysine | 2 | Cl | —SO$_2$CH$_3$ |
| lysine | 2 | Br | —SO$_2$CH$_3$ |
| tris(hydroxymethyl)aminomethane | 1 | Cl | Cl |

II. COMPOSITIONS AND METHODS

In certain embodiments, the invention relates to pharmaceutical composition comprising an IPM salt or analog thereof and a pharmaceutical diluent or excipient. In certain such embodiments, the pharmaceutical composition is a solution, preferably a saline solution comprising IPM or an IPM analog. In certain such embodiments, the concentration of the IPM salt or IPM analog salt in solution is from about 3 mg/mL to about 30 mg/mL or even greater. Such saline solutions may be prepared, for example, by dissolving a crystalline compound of formula (I) or a lyophilisate of IPM or an IPM analog as disclosed herein in a saline solution, e.g., while stirring at room temperature. In certain such embodiments, the saline solution is prepared such that the sodium chloride concentration is about 0.5%, 0.9%, 2.5%, 2.7%, 3.0%, 4.0%, or even 5.0%.

In certain embodiments, an aqueous solution may be prepared from a crystalline compound of formula I or a lyophilisate of IPM or an IPM analog as disclosed herein. Such an aqueous solution (e.g., in water or in an isotonic saline solution) is stable at room temperature for at least about 60 minutes, 80 minutes, 100 minutes, 120 minutes, 140 minutes, or even about 160 minutes at room temperature.

In certain embodiments, a crystalline compound of formula (I), such as a salt of IPM and Tris, has a solubility in water of at least about 30 mg/mL, 40 mg/mL, 50 mg/mL, 60 mg/mL, 70 mg/mL, or even 80 mg/mL. In certain embodiments a crystalline compound of formula (I), such as a salt of IPM and Tris, has a solubility in water of at least about at least about 200 mg/mL, at least about 500 mg/mL, at least about 800 mg/mL, at least about 1000 mg/mL, at least about 1200 mg/mL, or even at least 1400 mg/mL. In certain embodiments, the pH of a solution of the crystalline compound in water is between about 4.5 and about 10, such as between about 5.0 and 8.5, preferably between about 5.0 and about 7.0. In certain embodiments, the pH of such a solution is about 5.0.

In certain embodiments, the invention relates to a kit, comprising a crystalline compound of formula I and a saline solution.

The lyophilisates disclosed herein include IPM and IPM analogs that are formulated with one or more equivalents of a base. Because IPM and its analogs are acid labile and are acidic, the presently disclosed lyophilisates offer greater stability as well as other advantages. The advantages of the disclosed formulations in terms of synthesis, stability and bioavailability will be apparent to those of ordinary skill in the art upon consideration of the present disclosure. Additional advantages of the IPM and IPM analogs that are formulated with one or more equivalents of a base may include increased solubility in water or bodily fluids.

In certain embodiments, the disclosed lyophilisates are salts of isophosphoramide mustard or isophosphoramide mustard analogs including one or more cations. In certain embodiments, the cations can be a conjugate acid of an amine base or can be a quaternary ammonium cation. Suitable counterions for isophosphoramide mustard and its analogs include the conjugate acids (as used herein terms that refer to amines should be understood to include their conjugate acids unless the context clearly indicates that the free amine is intended) of bases including basic amino acids, aliphatic amines, heterocyclic amines, aromatic amines, pyridines, guanidines and amidines. Of the aliphatic amines, the acyclic aliphatic amines, and cyclic and acyclic di- and tri-alkyl amines are particularly suitable for use in the disclosed compounds. In addition, quaternary ammonium counterions are examples of suitable counterions that can be used. In certain embodiments, such a lyophilisate may further comprise an excipient. Suitable excipients include, but are not limited to, mannitol, anhydrous lactose, sucrose, D(+)-trehalose, dextran 40 and povidone (PVP K24).

In certain embodiments, the compounds and compositions, such as the lyophilisates disclosed herein, are stable at room temperature for at least two weeks, at least three weeks, at least a month, at least two months, at least three months, or even at least six months. In certain embodiments, the salts are stable at lower temperatures (e.g., 0° C., 2° C., 4° C., 6° C., etc.) for at least two weeks, at least three weeks, at least a month, at least two months, at least three months, or even at least six months. In certain such embodiments, the compounds and compositions, such as the lyophilisates, are stable for at least one month, at least two months, at least four months, or even at least six months at a lower temperature (e.g., between about 0° C. and about 20° C., between about 0° C. and about 10° C., or even between about 2° C. and about 8° C.). In certain embodiments, the lyophilisate comprises an IPM salt or an analog thereof. In certain embodiments, the lyophilisate comprises IPM•Tris or IPM•(LYS)$_2$, preferably IPM•Tris, and in particularly preferred embodiments, such compositions further comprise a bulking agent, such as mannitol.

In a further embodiment, the salts described above can include a second amine or ammonium group. In one embodiment, the lyophilisates disclosed herein include more than one equivalent of an amine for each equivalent of isophosphoramide mustard or isophosphoramide mustard analog. Such embodiments include those having non-integer ratios of amine to isophosphoramide mustard or isophosphoramide mustard analogs. In certain embodiments, the lyophilisates have a two to one or three to one ratio of amine to isophosphoramide mustard or an isophosphoramide mustard analog.

In working embodiments, salts were produced containing two equivalents of amine base per equivalent of isophosphoramide mustard. In certain embodiments, an amine base used to form isophosphoramide mustard and isophosphoramide mustard analog salts includes more than one amino group; such bases can be termed "multibasic." More specifically, certain examples of multibasic bases that can be used have two amino groups; such compounds can be referred to as "dibasic." For example, one suitable dibasic molecule is N,N-dimethylaminopyridine, which includes two basic amino groups. Certain embodiments of a lyophilisate disclosed herein include isophosphoramide mustard or an isophosphoramide mustard analog and one equivalent of a dibasic amine.

Certain isophosphoramide mustard and isophosphoramide mustard analog lyophilisates disclosed herein include two leaving groups. Without limitation to theory, it is believed that the two leaving groups are displaced in vivo by biomolecular nucleophiles, such as nucleic acids and proteins, thereby cross-linking the biomolecules. The term "leaving group" refers to a group that can be displaced by a nucleophile. With reference to the presently disclosed compounds, leaving group refers to a group that can be displaced to form an aziridinium intermediate, or can be directly displaced by a biomolecular nucleophile, such as a nucleic acid-nucleophile, to form, for example, a 7-alkylated guanidinium species. Examples of suitable leaving groups include the halogens and the sulfonates (—$SO_2R$). In one embodiment of the disclosed isophosphoramide analog salts, the compound is a "mixed" leaving group compound, including two different types of leaving groups, for example a halogen and a sulfonate or two different halogens, such as a bromide and a chloride. U.S. Pat. No. 6,197,760 to Struck teaches methods for making such mixed leaving group compounds.

In certain embodiments, lyophilisates of disclosed salts improve the reconstitutional stability as compared to a lyophilized preparation of isophosphoramide mustard itself. In certain such embodiments, a lyophilisate prepared from disclosed salts of IPM or an analog thereof and an excipient, such as from IPM or an analog thereof and Tris, optionally including an excipient, e.g., a bulking agent, such as mannitol, that has been reconstituted in a saline solution (preferably 5% sodium chloride) maintains >90% potency for at least about 30 minutes, 60 minutes, 90 minutes, 120 minutes, 140 minutes, or even at least about 160 minutes.

In certain such embodiments, dissolving a salt of IPM or an analog thereof, such as IPM•Tris, or a lyophilisate prepared from a salt of IPM or an analog thereof, such as IPM•Tris, and an optional excipient, e.g., a bulking agent, such as mannitol, in a saline solution maintains at least 96%, at least 97%, at least 98%, or even at least 99% purity for at least about 30 minutes, 60 minutes, 90 minutes, 3 hours, or even 4.5 hours or more at room temperature. In certain embodiments, such reconstituted solutions are more stable than reconstituted IPM•$(LYS)_2$ solutions under identical conditions. In certain such embodiments, the IPM•$(LYS)_2$ that has been reconstituted degrades at least 1.25 times as fast, at least 1.5 times as fast, at least twice as fast, or even at least three or four times as fast as the salt of IPM or analog thereof.

In certain embodiments where the lyophilisate comprises a salt of IPM or an analog thereof and an excipient, such as a lyophilisate comprising IPM or an analog thereof, Tris, and mannitol, the mixture has a solubility in water of at least about 30 mg/mL, 40 mg/mL, 50 mg/mL, 60 mg/mL, 70 mg/mL, or even 80 mg/mL.

In certain embodiments, lyophilisates of disclosed salts of IPM or an analog thereof are more stable than a lyophilized preparation of isophosphoramide mustard itself, i.e., as the free acid. In certain preferred such embodiments, the lyophilisate of the disclosed salts have a longer shelf life than a lyophilized preparation of isophosphoramide mustard itself, preferably at least twice as long, more preferably at least five times as long. In certain embodiments, the lyophilisate is formed from the Tris salt of IPM, which may or may not be crystalline prior to dissolution.

As described above, in certain embodiments, such lyophilisates further comprise an excipient, e.g., a bulking agent, preferably mannitol. In certain embodiments, the lyophilisate comprises a bulking agent selected from mannitol, anhydrous lactose, sucrose, D(+)-trehalose, dextran 40 and povidone (PVP K24), preferably mannitol. In certain embodiments, addition of such a bulking agent may improve the stability of the lyophilisate relative to the lyophilisate formulation in the absence of the bulking agent. In certain such embodiments, such a lyophilisate is stable at about –70° C., about –20° C., or even 5° C., e.g., over a period of one month, two months, three months, six months, nine months, one year, or even two years or more.

In certain such embodiments where the lyophilisate comprises a bulking agent, such as mannitol, the lyophilisate comprises from about 1% to about 10%, or about 1% to about 5% (w/v) bulking agent, e.g., mannitol. Prior to lyophilisation or upon reconstitution, such compositions may comprise from about 15 mg/mL to about 25 mg/mL of IPM, and/or an amine such as Tris in a concentration of about 0.5 to about 1.5 M, preferably in a roughly equimolar amount relative to the IPM. In certain embodiments, when preparing the solution prior to lyophilisation, instead of adding IPM and amine, such as Tris, as separate components, they are added together in the form of a crystalline IPM•Tris salt as disclosed herein.

In certain embodiments, the invention relates to a kit, comprising a lyophilisate as disclosed herein and a saline solution.

The compounds disclosed herein may be administered orally, topically, transdermally, parenterally, via inhalation or spray and may be administered in dosage unit formulations containing conventional non-toxic pharmaceutically acceptable carriers, adjuvants and vehicles.

In certain embodiments, parenteral administration of the disclosed IPM salts and analogs thereof via injection is preferred. In certain embodiments, oral administration of the disclosed IPM salts and analogs thereof is preferred. In certain embodiments, orally (PO) administered IPM salts and analogs thereof show pharmacokinetic (PK) parameters similar to those observed with intravenous (IV) administration. The agents may be provided in a single dosage or chronically, dependent upon the particular disease, condition of patient, toxicity of compound and other factors as will be recognized by a person of ordinary skill in the art.

The therapeutically effective amount of the compound or compounds administered can vary depending upon the desired effects and the factors noted above.

Pharmaceutical compositions for administration to a subject can include carriers, thickeners, diluents, buffers, preservatives, surface active agents and the like in addition to the molecule of choice. Pharmaceutical compositions can also include one or more additional active ingredients such as antimicrobial agents, anti-inflammatory agents, anesthetics, and the like. Pharmaceutical formulations can include additional components, such as carriers. The pharmaceutically acceptable carriers useful for these formulations are conventional. Remington's Pharmaceutical Sciences, by E. W. Martin, Mack Publishing Co., Easton, Pa., 21st Edition (2006), describes compositions and formulations suitable for pharmaceutical delivery of the compounds herein disclosed.

In general, the nature of the carrier will depend on the particular mode of administration being employed. For instance, parenteral formulations usually contain injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

In certain embodiments, a disclosed compound is formulated as an oral dosage form, such as a pill, tablet, or capsule. In certain embodiments, the oral dosage form is a capsule.

In certain embodiments, such oral dosage forms comprise at least one excipient, glidant, diluent, lubricant, and/or disintegrant. In certain such embodiments, suitable excipients, glidants, diluents, lubricants, and/or disintegrants include, but are not limited to, talc, fumed silicon dioxide, starch, calcium silicate, magnesium carbonate, magnesium oxide, magnesium lauryl sulfate, sodium lauryl sulfate, lactose, microcrystalline cellulose, hydroxypropylmethyl cellulose, dextrose, glucose, sucrose, starch, starch derivatives, calcium carbonate, dibasic calcium phosphate, magnesium carbonate, magnesium stearate, calcium stearate, sodium stearyl fumarate, polyethylene glycol 4000, polyethylene glycol 6000, sodium benzoate, light mineral oil, hydrogenated vegetable oils, stearic acid, glyceryl behenate, insoluble ion exchange resins, sodium starch glycolate, sodium carboxymethylcellulose (croscarmellose sodium), gums (e.g., agar, guar, xanthan), alginic acid, sodium alginate, and crospovidone.

In certain such embodiments, the oral dosage form comprises a compound as disclosed herein and at least one excipient, glidant, diluent, lubricant, and/or disintegrant; preferably at least one excipient, glidant, diluent, lubricant, and/or disintegrant that is suitable for formulation with a hygroscopic active agent. In certain such embodiments, the oral dosage form comprises at least one excipient, glidant, diluent, lubricant, and/or disintegrant selected from microcrystalline cellulose, lactose, sodium carboxymethylcellulose, magnesium stearate, dibasic calcium phosphate, sodium starch glycolate, hydroxypropylmethyl cellulose and mannitol.

In certain embodiments, a disclosed compound is formulated for administration to a human subject. In aspect of this embodiment the pharmaceutical composition includes from about 0.1 mg/mL to about 250 mg/mL, such as from about 20 to about 100 mg/mL of the compound of an IPM salt or analog thereof.

In one aspect, certain embodiments of pharmaceutical compositions are formulated into unit dosage forms. For example such unit dosage forms can contain from about 1 mg to about 100 mg or 100 mg to about 1500 mg, such as from about 5 mg to about 200 mg or 200 mg to about 1500 mg of a disclosed IPM salt or analog thereof per dosage unit. In certain embodiments, a dosage unit may comprise about 15 mg, about 30 mg, about 45 mg, about 60 mg, about 75 mg, or even about 77 mg of a disclosed IPM salt or analog thereof.

It is specifically contemplated in some embodiments that the present compounds are delivered via an injected and/or implanted drug depot, for instance comprising multi-vesicular liposomes such as in DepoFoam (SkyePharma, Inc, San Diego, Calif.) (see, for instance, Chamberlain et al. Arch. Neuro. 1993, 50, 261-264; Katri et al. J. Pharm. Sci. 1998, 87, 1341-1346; Ye et al., J. Control Release 2000, 64, 155-166; and Howell, Cancer J. 2001, 7, 219-227).

Methods are disclosed herein for treating conditions characterized by abnormal or pathological proliferative activity or neoplasia by administering one or more of the disclosed compounds and compositions to a subject.

Conditions that can be treated according to the disclosed method include those characterized by abnormal cell growth and/or differentiation, such as cancers and other neoplastic conditions. Typical examples of proliferative disorders that can be treated using the disclosed compounds and compositions are listed below.

Examples of hematological tumors that can be treated using the compounds and compositions disclosed herein include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Additional examples of conditions that may be treated using the disclosed compounds and compositions include solid tumors, such as sarcomas and carcinomas, include fibrosarcoma, myxosarcoma, liposarcoma, chondrosarcoma, osteogenic sarcoma, cyclophosphamide (CPA)-resistant sarcomas, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, bladder carcinoma, and CNS tumors (such as a glioma, astrocytoma, medulloblastoma, craniopharyogioma, ependymoma, pinealoma, hemangioblastoma, acoustic neuroma, oligodendroglioma, menangioma, melanoma, neuroblastoma and retinoblastoma).

In certain embodiments the compounds disclosed herein are superior to CPA or Ifos alone against CPA and/or Ifos resistant tumor growth. Therefore one aspect of a method disclosed herein includes treating a subject having a CPA and/or Ifos resistant neoplastic condition with an IPM salt or analog thereof disclosed herein.

In some embodiments, the compounds disclosed herein exhibit reduced toxicity as compared to CPA and/or Ifos. For example, high doses of CPA and/or Ifos may result in increased kidney, bladder, and/or central nervous system toxicities due to the presence of certain metabolites, such as chloroacetaldehyde and acrolein. In some embodiments, the present compounds reduce or avoid production of these or other toxic metabolites while retaining efficacy. The present compounds thus are able to provide therapeutic treatment while reducing deleterious side-effects, such as normal kidney, bladder, or central nervous system cell death, that may be linked to metabolites of CPA and/or Ifos. Accordingly, the present compounds are useful as substitutes for CPA and/or Ifos.

For example, the present compounds are useful in preparing patients for blood cell and bone marrow transplants. CPA and Ifos are often used in blood cell and bone marrow transplants, and the present compounds represent an advantageous alternative, for example, due to the present compounds' reduced toxicity profile and/or increased potency. Additionally, the present compounds may also be employed in blood cell and bone marrow transplants wherein CPA and Ifos are inappropriate, for example, where high doses of CPA and Ifos prove too toxic. The present compounds may be administered minutes, hours, days, weeks, or months prior to the transplant, particularly days or weeks prior to the transplant. Moreover, the present compounds may be administered in single, multiple, and/or repeating dosage forms and/or in association with other agents in preparation of the blood cell or bone marrow transplant.

In certain embodiments, the present compounds are useful in conditioning regimens for blood cell and bone marrow transplants, for example, as substitutes for CPA and/or Ifos. Moreover, the present compounds can be administered without using protective measures, such as mesna and/or intravenous hydration that are often used in association with CPA and Ifos.

In another embodiment, the present compounds may be used in combination with CPA and/or Ifos, for example, in preparing patients for blood cell and bone marrow transplants and in conditioning regimens for blood cell and bone marrow transplants. Compositions comprising one or more of the present compounds in combination with CPA and/or Ifos offer additional benefits, such as reduced toxicity and/or increased potency, over CPA and/or Ifos alone.

In certain embodiments of the method a subject is administered from about 0.2 mg/kg/day to about 20 mg/kg/day of a disclosed IPM salt or analog thereof. For example, from about 0.5 to about 10 mg/kg/day, such as from about 1 to about 7.5 mg/kg/day of a disclosed compound can be administered to a subject.

In certain embodiments, IPM, an analog or a salt thereof is administered to a subject at a dose (e.g., daily dose) greater than about 1.0 g, greater than about 1.5 g, greater than about 2.0 g, or even greater than about 2.5 g. In certain embodiments, the IPM salt is IPM•Tris, e.g., up to about 2.0 g, 2.5 g, or even 3.0 g.

In certain embodiments, IPM or an analog thereof is administered to a subject as a salt such that the dose (e.g., daily dose) of IPM or the analog thereof (i.e., taking into account only the IPM anion of the salt and discounting the weight of the counterion or other components of the composition) is greater than about 0.4 g, greater than about 0.6 g, greater than about 0.8 g, or even greater than about 1.0 g. In certain embodiments, IPM is administered in a composition as disclosed herein at a dose greater than about 0.4 g, greater than about 0.6 g, greater than about 0.8 g, or even greater than about 1.0 g, e.g., up to about 2.0 g, 2.5 g, or even 3.0 g.

In certain embodiments, a course of an IPM salt or analog thereof may comprise a total amount of IPM or analog thereof (i.e., taking into account only the IPM anion of the salt and discounting the weight of the counterion or other components of the composition) that is greater than about 0.8 g, greater than about 1.0 g, greater than about 1.5 g, or even greater than about 2.0 g.

In certain embodiments, a dose of IPM salt or analog thereof may be administered from once a week, three times a week, five times a week, once a day, or even twice a day, preferably once a day. In certain such embodiments, a course of an IPM salt or analog thereof may be administered, where a course is two or more consecutive doses. In certain embodiments a course of treatment may comprise administering a dose of an IPM salt or analog thereof once a day for two, three, four or even five days, preferably three days. Such doses may be on consecutive or non-consecutive days.

In certain embodiments, a single dose (e.g., a daily dose) may comprise more than one dosage form, e.g., a single dose may comprise two or more capsules, tablets, or pills. In certain embodiments, a daily dose comprising multiple dosage forms may be administered all at once, or subsets of the dosage forms may be administered at intervals throughout the day.

In another embodiment of the method, a subject is administered a dose (e.g., a daily dose) from about 1 to about 1500 mg/m$^2$, such as from about 1 to about 700 mg/m$^2$, about 5 to about 1000 mg/m$^2$, about 5 to about 700 mg/m$^2$, about 5 to about 500 mg/m$^2$, about 600 to about 1200 mg/m$^2$, about 100 to about 1500 mg/m$^2$, about 30 to about 600 mg/m$^2$, about 10 to about 600 mg/m$^2$, or from about 10 to about 100 mg/m$^2$ of an IPM salt or analog thereof as disclosed herein. For example, about 10 mg/m$^2$, about 12, or even 14 mg/m$^2$.

In certain embodiments of the method for treating hyperproliferative disorders disclosed herein, a disclosed compound is administered to a subject on a multiple daily dosing schedule. In such embodiments the compound is administered on at least two days and on as many as five different days. In one aspect of multiple daily dosing schedules, the compound is administered to the subject on consecutive days, such as from two to five consecutive days. Alternatively, the compound is administered to the subject on non-consecutive days, such every other day.

In certain embodiments of the method one or more additional therapeutic agents is administered to a subject in addition to the presently disclosed compounds and compositions. For example, additional therapeutic agents can that can be used include microtubule binding agents, DNA intercalators or cross-linkers, DNA synthesis inhibitors, DNA and/or RNA transcription inhibitors, antibodies, enzymes, enzyme inhibitors, gene regulators, and/or angiogenesis inhibitors.

Microtubule binding agent refers to an agent that interacts with tubulin to stabilize or destabilize microtubule formation thereby inhibiting cell division. Examples of microtubule binding agents that can be used in conjunction with IPM, an analog, or a salt thereof include, without limitation, paclitaxel, docetaxel, vinblastine, vindesine, vinorelbine (navelbine), the epothilones, colchicine, dolastatin 15, nocodazole, podophyllotoxin and rhizoxin. Analogs and derivatives of such compounds also can be used and will be known to those of ordinary skill in the art. For example, suitable epothilones and epothilone analogs for incorporation into the present compounds are described in International Publication No. WO 2004/018478, which is incorporated herein by reference. Taxoids, such as paclitaxel and docetaxel are currently believed to be particularly useful as therapeutic agents in the presently disclosed compounds. Examples of additional useful taxoids, including analogs of paclitaxel are taught by U.S. Pat. Nos. 6,610,860 to Holton, 5,530,020 to Gurram et al. and 5,912,264 to Wittman et al., each of which is incorporated herein by reference in its entirety.

Suitable DNA and/or RNA transcription regulators, including, without limitation, actinomycin D, daunorubicin, doxorubicin and derivatives and analogs thereof also are suitable for use in combination with the presently disclosed compounds.

DNA intercalators and cross-linking agents that can be incorporated into the disclosed compounds include, without limitation, cisplatin, carboplatin, oxaliplatin, mitomycins, such as mitomycin C, bleomycin, chlorambucil, cyclophosphamide and derivatives and analogs thereof.

DNA synthesis inhibitors suitable for use as therapeutic agents include, without limitation, methotrexate, 5-fluoro-5'-deoxyuridine, 5-fluorouracil and analogs thereof.

Examples of suitable enzyme inhibitors for use in combination with the presently disclosed compounds include, without limitation, camptothecin, etoposide, formestane, trichostatin and derivatives and analogs thereof.

Suitable therapeutics for use with the presently disclosed compounds that affect gene regulation include agents that result in increased or decreased expression of one or more genes, such as, without limitation, raloxifene, 5-azacytidine, 5-aza-2'-deoxycytidine, tamoxifen, 4-hydroxytamoxifen, mifepristone and derivatives and analogs thereof.

Angiogenesis inhibitors are known in the art and examples of suitable angiogenesis inhibitors include, without limitation, angiostatin K1-3, staurosporine, genistein, fumagillin, medroxyprogesterone, suramin, interferon-alpha, metalloproteinase inhibitors, platelet factor 4, somatostatin, thrombospondin, endostatin, thalidomide, and derivatives and analogs thereof.

Other therapeutic agents, particularly anti-tumor agents, that may or may not fall under one or more of the classifications above, also are suitable for administration in combination with the presently disclosed compounds. By way of example, such agents include adriamycin, apigenin, rapamycin, zebularine, cimetidine, and derivatives and analogs thereof.

In certain embodiments, the IPM salt or analog thereof is administered in combination with a DNA and/or RNA transcription regulator such as doxorubicin. In certain alternative embodiments, the IPM salt or analog thereof is administered in combination with a microtubule binding agent such as docetaxel or paclitaxel.

In certain embodiments, combinations as described herein may be synergistic in nature, meaning that the therapeutic effect of the combination of the IPM salt or analog thereof and the other therapeutic agent(s) is greater than the sum of the individual effects when the two or more agents are administered separately in the same amount.

In certain such embodiments, such a synergistic effect may permit administration of sub-therapeutic doses of the IPM salt or analog thereof. In certain such embodiments, administration of a sub-therapeutic dose may reduce or avoid a side-effect associated with higher doses of the IPM salt or analog thereof, e.g., the methods of the present invention may be advantageous over existing combination therapies by allowing conventional anti-cancer agents to exert greater effect at lower dosage.

In certain embodiments, the efficacy of the additional agent is improved when administered in combination with an IPM salt or analog thereof. In certain such embodiments, the additional agent is a chemotherapeutic, including, but not limited to, microtubule binding agents, DNA intercalators or cross-linkers, DNA synthesis inhibitors, DNA and/or RNA transcription inhibitors, antibodies, enzymes, enzyme inhibitors, gene regulators, and/or angiogenesis inhibitors. In certain such embodiments, the efficacy of a microtubule binding agent, such a docetaxel or paclitaxel, is improved when administered in combination with an IPM salt or analog thereof. In certain alternative such embodiments, the efficacy of a DNA and/or RNA transcription inhibitor, such as doxorubicin, is improved when administered in combination with an IPM salt or analog thereof. In certain embodiments, the IPM salt or analog thereof is IPM•Tris.

As used herein, the term "sub-therapeutic dose" includes a dose that may stabilize or reduce tumor volume, but would not be considered an effective treatment at that dose, or even a dose that alone provides no measurable therapeutic effect.

In certain embodiments, the IPM salt or analog thereof is administered at a dose of about 100 mg to about 500 mg, about 150 mg to about 400 mg, or even about 175 mg to about 300 mg. In certain embodiments, the IPM salt or analog thereof is administered at a dose of about 150 mg, about 175 mg, about 185 mg, about 190 mg, about 200 mg, about 225 mg, about 250 mg, about 275 mg, about 285 mg, about 290, or even about 300 mg. In certain such embodiments the IPM salt or analog thereof that is administered at such doses is administered orally.

In certain such embodiments the IPM salt or analog thereof that is administered in combination with doxorubicin at a dose of about 100 mg to about 200 mg, about 110 mg to about 180 mg, or even about 115 to about 150 mg. In certain such embodiments the IPM salt or analog thereof that is administered in combination with doxorubicin at a dose of about 100 mg, about 110 mg, about 115 mg, about 125 mg, about 135 mg, about 140 mg, about 145 mg, about 155 mg, about 165 mg, about 175 mg, about 185 mg, or even about 200 mg.

In certain such embodiments the IPM salt or analog thereof that is administered in combination with docetaxel at a dose of about 50 mg to about 200 g, about 75 mg to about 195 mg, or even about 80 to about 190 mg. In certain such embodiments the IPM salt or analog thereof that is administered in combination with docetaxel at a dose of about 50 mg, about 70 mg, about 80 mg, about 90 mg, about 95 mg, about 100 mg, about 110 mg, about 120 mg, about 130 mg, about 140 mg, about 150 mg, about 160 mg, about 170 mg, about 180 mg, about 190 mg, or even about 200 mg.

III. DEFINITIONS

The following explanations of terms and examples are provided to better describe the present compounds, compositions and methods, and to guide those of ordinary skill in the art in the practice of the present disclosure. It is also to be understood that the terminology used in the disclosure is for the purpose of describing particular embodiments and examples only and is not intended to be limiting.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

The term "acyclic aliphatic amine" refers to an aliphatic amine as above, wherein at least one of the aliphatic groups is acyclic.

As used herein, "aliphatic amine" refers to a compound of the formula $NR^1R^2R^3$, wherein at least one of $R^{1-3}$ is an aliphatic group.

The term "angiogenesis inhibitor" is used herein, to mean a molecule including, but not limited to, biomolecules, such as peptides, proteins, enzymes, polysaccharides, oligonucleotides, DNA, RNA, recombinant vectors, and small molecules that function to inhibit blood vessel growth. Angiogenesis is implicated in certain pathological processes, such as those involved in disorders such as diabetic retinopathy, chronic inflammatory diseases, rheumatoid arthritis, dermatitis, psoriasis, stomach ulcers, and most types of human solid tumors.

The term "heterocyclic amine" refers to a compound of the formula $NR^1R^2R^3$, wherein at least one of $R^{1-3}$ is a heterocyclic group or $R^1$, $R^2$ and/or $R^3$ taken together with their common nitrogen atom form a ring.

The term "leaving group" refers to a group that can be displaced by a nucleophile. With reference to the presently disclosed compounds, leaving group refers to a group that can be displaced to form an aziridinium intermediate, or can be directly displaced by a biomolecular nucleophile, such as a nucleic acid nucleophile, to form, for example, a 7-alkylated guanidinium species. Examples of suitable leaving groups include the halogens and the sulfonates (—$SO_2R$). In certain embodiments of the disclosed isophosphoramide analog salts, the compound is a "mixed" leaving group compound, including two different types of leaving groups, for example a halogen and a sulfonate or two different halogens, such as a bromide and a chloride. U.S. Pat. No. 6,197,760 to Struck teaches methods for making such mixed leaving group compounds.

"Neoplasia" refers to the process of abnormal and uncontrolled cell growth. Neoplasia is one example of a proliferative disorder. The product of neoplasia is a neoplasm (a tumor), which is an abnormal growth of tissue that results from excessive cell division. A tumor that does not metastasize is referred to as "benign." A tumor that invades the surrounding tissue and/or can metastasize is referred to as "malignant."

"Optional" or "optionally" means that the subsequently described event or circumstance can but need not occur, and that the description includes instances where said event or circumstance occurs and instances where it does not.

As used herein, the term stable means that the compound does not degrade more than 5%, preferably not more than 2% or even 1% over at least five days, or the period of time specified. Such degradation can be monitored by $^1$H NMR, HPLC, or other suitable means.

As used herein, and as well understood in the art, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

IV. EXAMPLES

The foregoing disclosure is further explained by the following non-limiting examples.

Example 1

Figure 2:
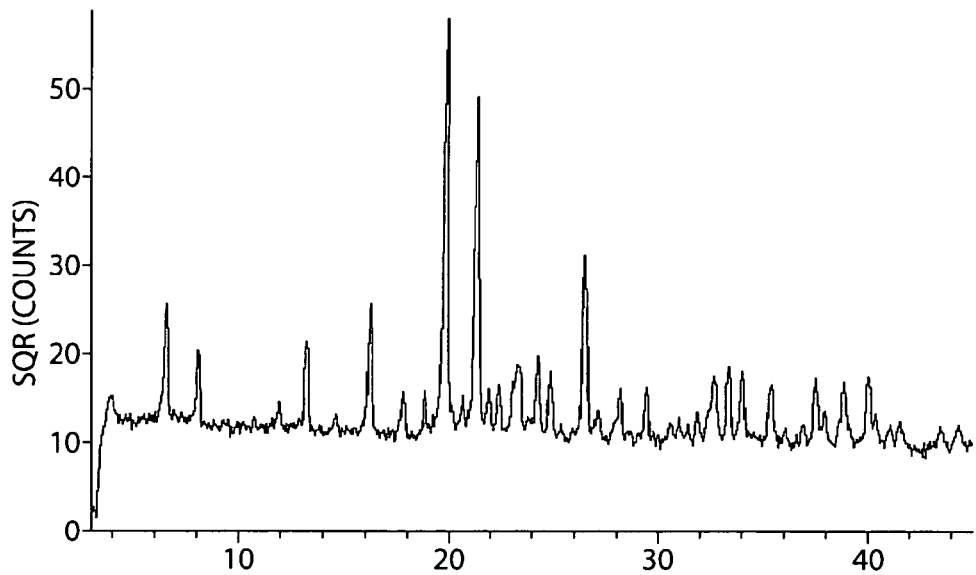
FIG. 2 shows the X-ray powder diffraction of IPM•Tris.
Figure 3:
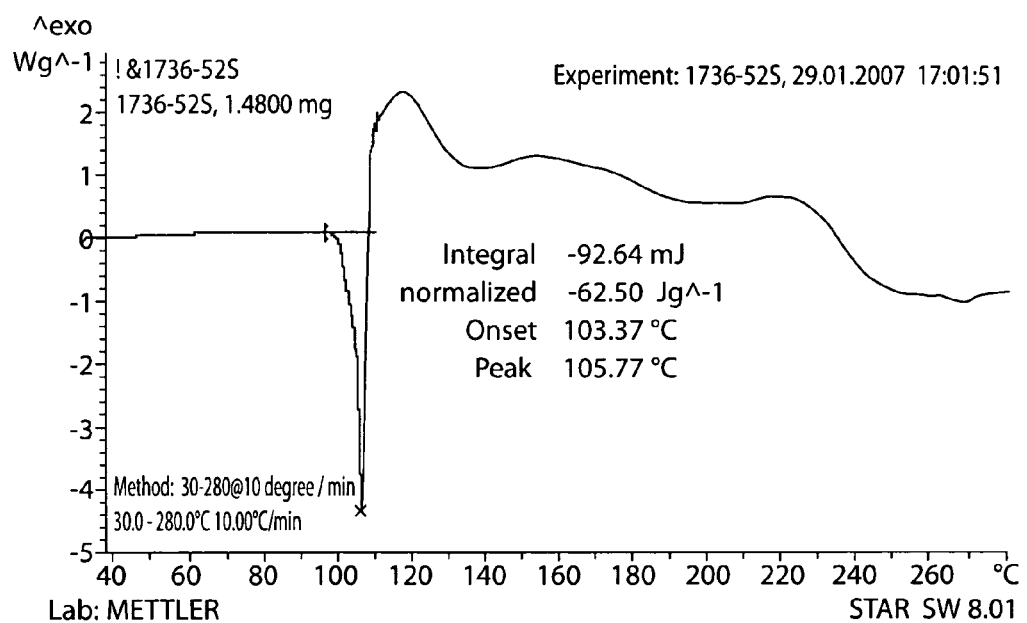
FIG. 3 shows differential scanning calorimetry (DSC) of IPM•Tris.
Figure 4:
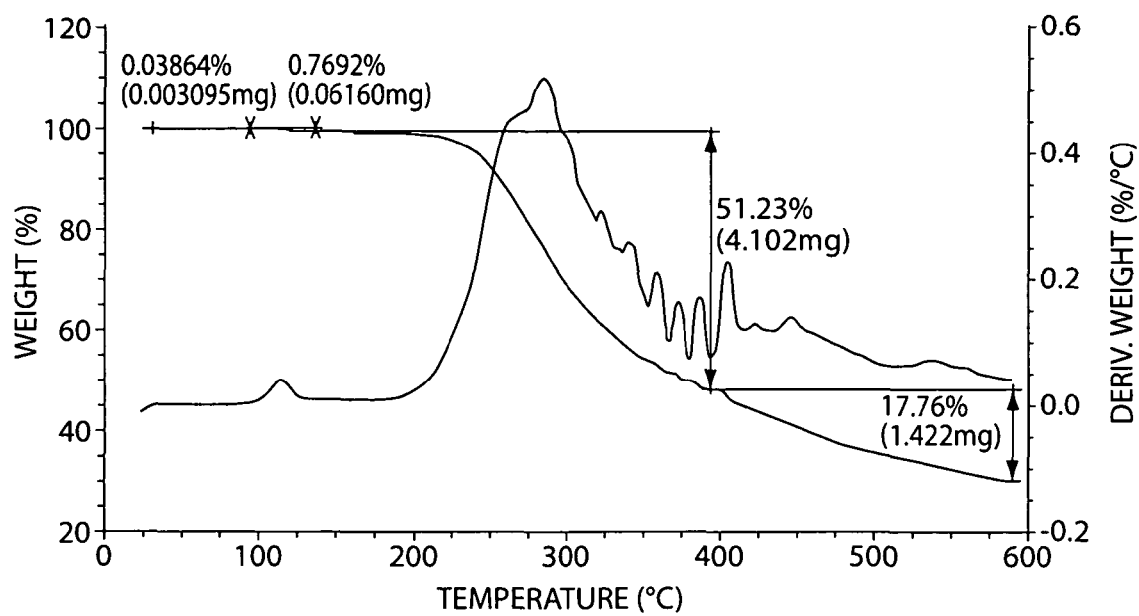
FIG. 4 shows thermogravimetric analysis (TGA) of IPM•Tris.
Figure 5:
FIG. 5 shows scanning electron microscope (SEM) images of crystalline IPM•Tris.

A reactor was charged with Tris (103.3 mg) and MeCN (3 mL) followed by addition of IPM (200.5 mg) in MeCN (3 mL). The reaction mixture was stirred overnight. The solid was then collected by filtration and the cake was washed with MeCN. The cake was dried under vacuum to constant weight to provide the final product (296 mg). The final product was subjected to X-ray powder diffraction to confirm crystallinity (FIG. 2). The crystallinity was further supported by DSC where a sharp peak appeared at 105.77 (FIG. 3). Additionally, the IPM•Tris salt showed a weight loss of 0.7692% around 125° C. by TGA (FIG. 4). Finally, SEM showed that IPM•Tris had a plate-like crystal shape.

The stability of the crystalline IPM•Tris was monitored by $^1$H NMR and was found to remain stable at room temperature for up to six days. The stability of the crystal structure was monitored by DSC which indicated that the IPM•Tris crystals had not absorbed water or changed in structure over the course of ten days at room temperature.

Example 2

A reactor was charged with Tris (8.563 g) and DMF (40 mL) and heated to form a clear solution. After the solution had cooled to room temperature, IPM was added. The mixture was stirred to form a clear solution. Acetonitrile (40 mL) and a small amount of seeds were then added to the solution, followed by the slow addition of MTBE (240 mL) to give a slurry. The slurry was stirred for another hour at which time the precipitate was collected by filtration, and the filter cake was washed with MTBE (80 mL). The filter cake was dried under vacuum to constant weight at room temperature to provide the final product (23.2 g).

Example 3

Figure 6:
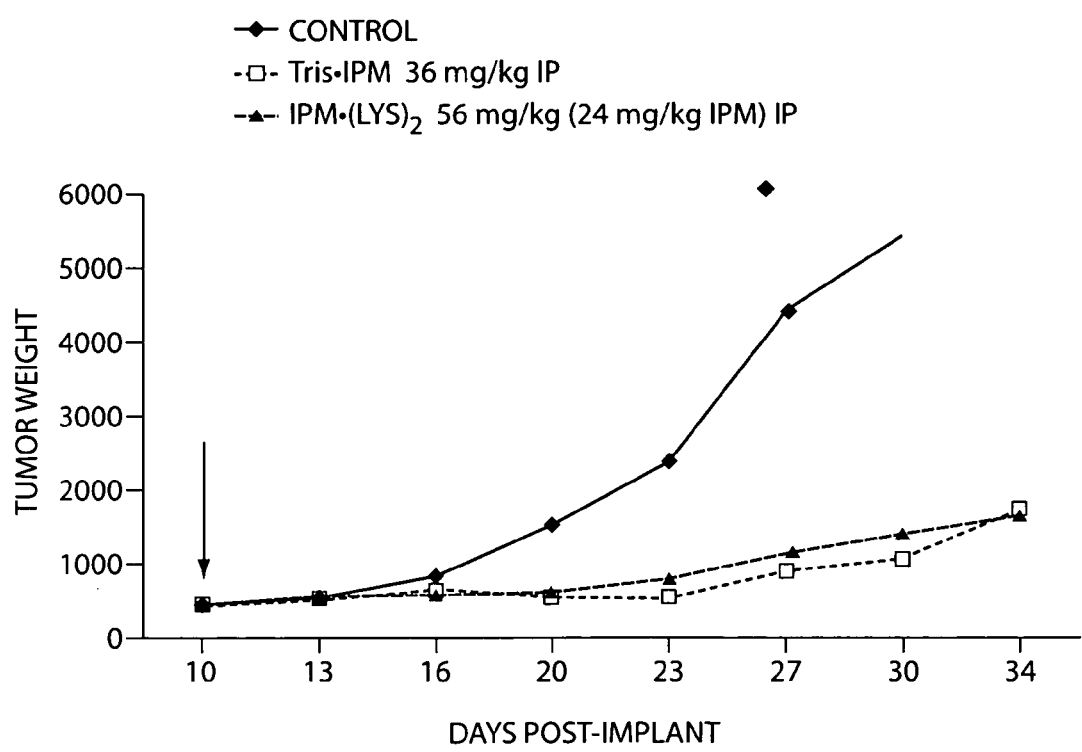
FIG. 6 shows a comparison of IPM•(LYS)$_2$ with IPM•Tris in human MX-1 breast cancer xenografts.

30 to 40 mg fragments of MX-1 human mammary tumors from an in vivo passage were implanted subcutaneously in nu/nu mice in the mammary fat pad and allowed to reach 75-200 mg in weight before the start of treatment. Treatment was initiated on Day 10 following tumor implantation; administration was intraperitoneal once daily for 5 days. IPM•(LYS)$_2$ (43% IPM and 57% Lys) and IPM•Tris showed similar activity against MX-1 tumors when doses were normalized to IPM (see FIG. 6).

Example 4

Figure 7:
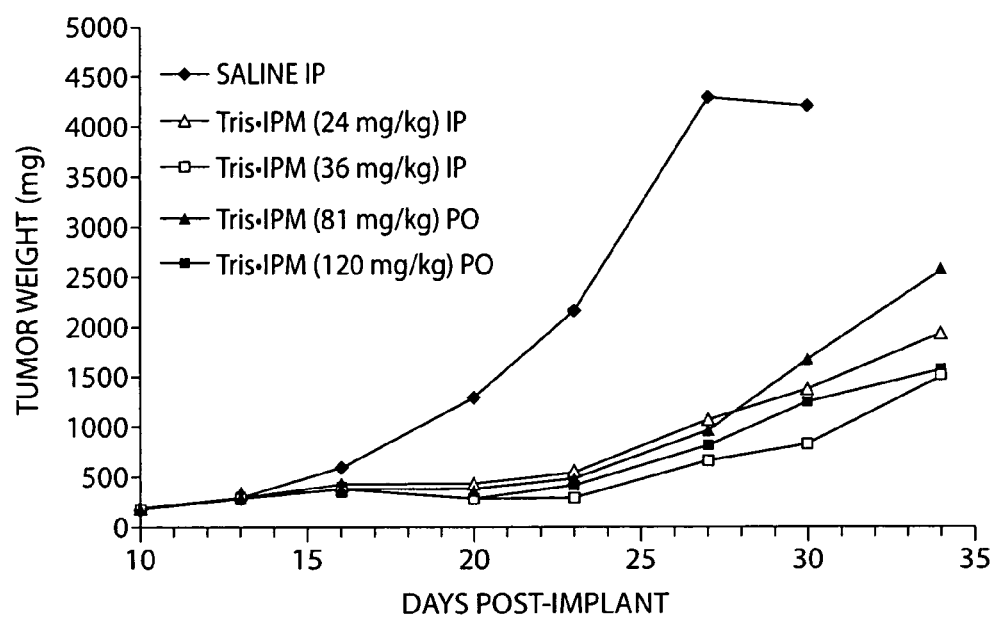
FIG. 7 shows a comparison of anti-tumor activity of IP and oral administration of IPM•Tris in human MX-1 breast cancer xenografts.
Figure 8A:
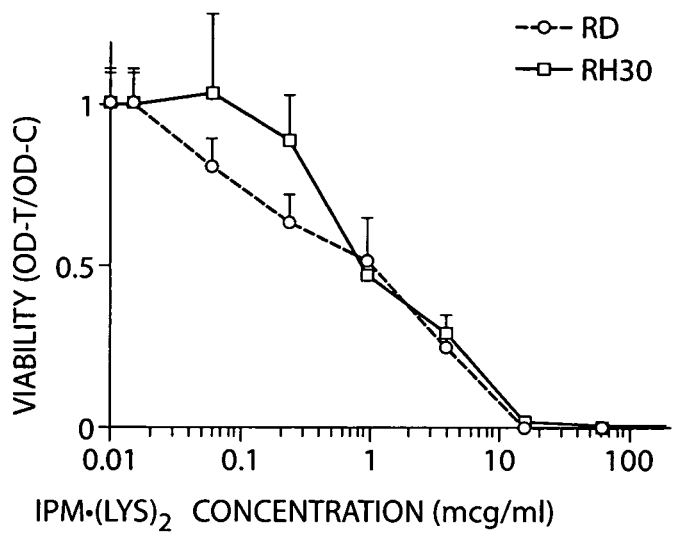
FIG. 8a shows the viability of RD and RH30 rhabdomyosarcoma cells when treated with IPM•(LYS)$_2$ at various concentrations.
Figure 8B:
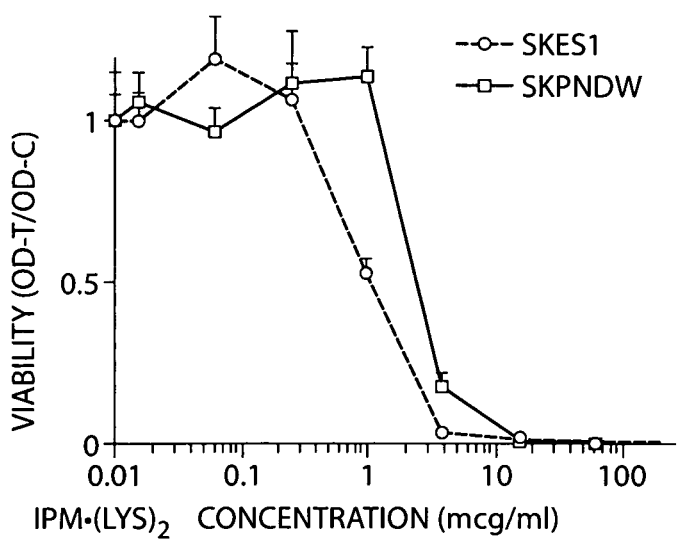
FIG. 8b shows the viability of SKES1 and SKPNDW Ewing's sarcoma cells when treated with IPM•(LYS)$_2$ at various concentrations.
Figure 8C:
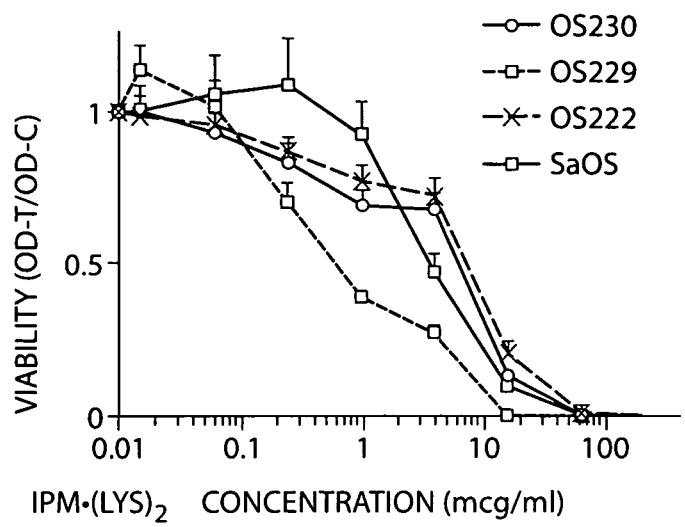
FIG. 8c shows the viability of OS230, OS229, OS222, and SaOS osteosarcoma cells when treated with IPM•(LYS)$_2$ at various concentrations.
Figure 8D:
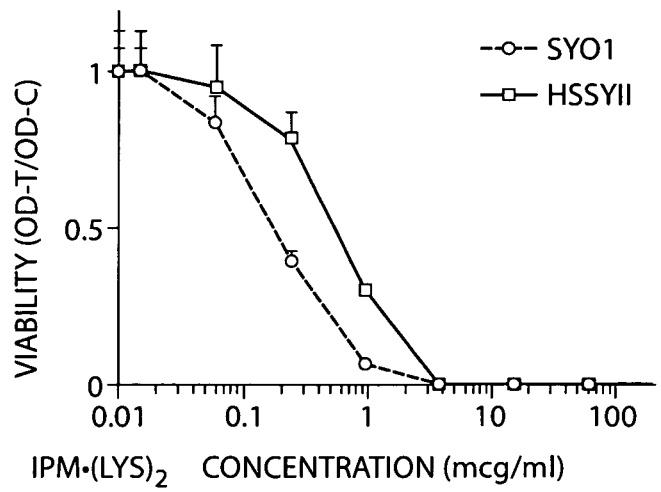
FIG. 8d shows the viability of SYO1 and HSSYII synovial sarcoma cells when treated with IPM•(LYS)$_2$ at various concentrations.

30 to 40 mg fragments of MX-1 human mammary tumors from an in vivo passage were implanted sc in nu/nu mice in the mammary fat pad and allowed to reach 75-200 mg in weight before the start of treatment. Treatment was initiated on Day 10 following tumor implantation; administration was intraperitoneal or orally once daily for 5 days. IPM•Tris, which may be prepared as described in Example 1, at maximum tolerated doses for each administration, was equally active against MX-1 tumors when administered orally or systemically (see FIG. 7).

Example 5

Cell Proliferation Assay

Growth inhibition was determined by the microculture tetrazolium method. Briefly, cells were seeded in 96-well flat-bottomed microtitre plates at a density of 500 cells/well in 100 µL of media. After overnight incubation, 100 µL of media containing IPM•(LYS)$_2$ was added to achieve specified final concentrations and a final volume of 200 µL/well. Data points represent the mean viability and the error bars (standard deviation of each experiment done in triplicate). At 120 hours the relative metabolic activities of treated and untreated cells were measured by mitochondrial conversion of 3-[4,5-dimethylthiazon-2-yl]-2,5-diphenyl tetrazolium bromide (MTT, Sigma, St. Louis, Mo.) to formazine. At the completion of the drug treatment, 250 µg of MTT was added to each well and incubated at 37° C., 5% $CO_2$ for 6 hours. Formazine crystals were dissolved in DMSO and optical density at 595 nm measured on a VERSAmax spectrophotometer (Molecular Devices, Sunnyvale, Calif.). Viability was defined as the absorbance at 595 nm in the treated samples divided by the absorbance at 570 nm in the control samples. The $IC_{50}$ was defined as the concentration at which viability of the treated cells was 50% that of the controls (treated/control=0.5).

Murine Xenograft Models

CB17 female scid*/* mice (Taconic Farms, Germantown, N.Y.) were implanted with tumor subcutaneous flank tumors. The OS31 tumor line was established at St. Judes Children's Cancer Research Hospital and has been described previously (20). For transplantation with OS1 tumor, mice were anesthetized with 4% isoflurane. After a small incision was made in the flank of the mouse, and a 4 mm by 4 mm section of tumor implanted subcutaneously.

CB17 female scid*/* mice (Taconic Farms, Germantown, N.Y.) were treated with IPM•(LYS)$_2$ daily for 1 or 3 days via tailvein injection starting on day 1 every 21 days for 2 cycles. Five non-tumor-bearing mice were assigned to each treatment group. Mice were treated with either 75 mg/kg/day, 100 mg/kg/day, 150 mg/kg/day, or 200 mg/kg/day of IPM•(LYS)$_2$. A toxic event was defined as weight loss greater than or equal to 20% the animal's weight at the time of randomization, or death. The MTD is defined as the highest dose at which no toxicity occurred.

When the tumors were approximately 0.20 to 0.7 cm in diameter, tumor-bearing mice were randomized into groups of 5 to 8 mice with 1 treatment group and 1 control group. Treated mice received tasidotin at a dose of 90 mg/kg/day as an intraperitoneal injection daily for 5 days starting on days 1 and 21. Assuming a spherical tumor, the volume was determined by the formula: $mm^3 = */6(D)d^2$, where D is the maximal diameter and d is the diameter perpendicular to D. Volumes are expressed as relative tumor volumes (RTV) where the tumor volume at any given time point is divided by the starting tumor volume. The RTV for treated and control mice were measured a minimum of once per week.

Assessment of Tumor Response and Statistical Considerations in Mice

Using criteria defined previously by Houghton, et al. progressive disease is defined as less than 50% regression from original tumor volume for the entire study period (RTV>0.5) and greater than 25% increase in tumor volume at the end of the study period (RTV>1.25). Stable disease tumor regression that does not exceed 50% of the original tumor volume throughout the entire study period (RTV>0.5) and less than 25% increase in tumor volume at the end of the study period (RTV<1.25). A partial response is defined as greater than 50% regression in tumor volume (RTV<0.5) but with a measurable tumor mass of greater than 0.10 cm$^3$. Loss of measurable tumor mass (<0.10 cm$^3$) at any point during the treatment period (6 weeks) was defined as a complete response (CR). A sustained CR was defined as a loss of measurable tumor mass (<0.10 cm$^3$) at any point after initiation of therapy without re-growth during the 6 week study period. Mice that died before week 9 or before the tumor reached 4 times the initial volume were excluded.

Statistical analysis was based on event-free survival (EFS). An event is defined as a relative tumor volume of 4× (i.e., quadruple the starting tumor size), or death. EFS is defined as the time from the initiation of the study to an event. For those tumors not reaching an event by 6 weeks, the end of the study period, the EFS time was excluded at that time. The exact log-rank test was used to compare event-free survival distributions between treatment and control groups. Additionally, the day 22 RTVs for the control and treated mice were compared using the Wilcoxian-Mann-Whitney test. This allows for comparison of tumor volume after one cycle of tasidotin and at or near the time of event for the untreated mice.

Biological Data

Figure 9A:
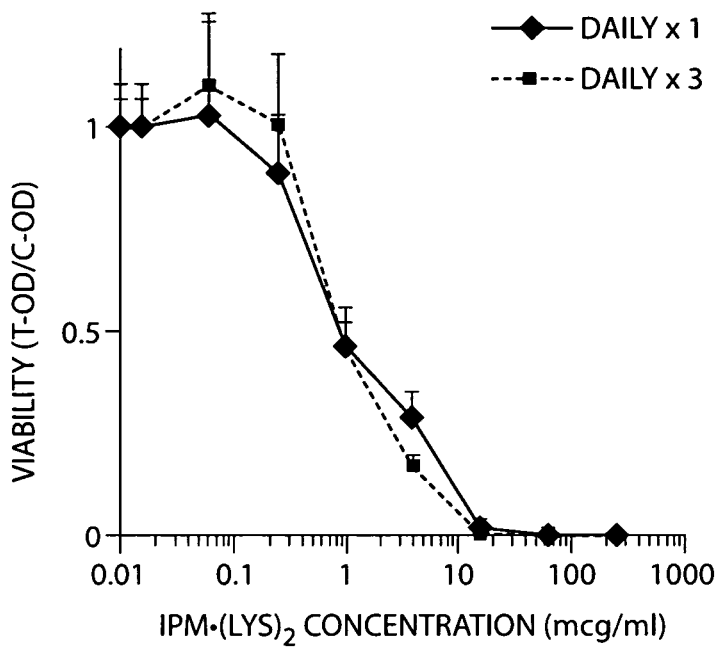
FIG. 9a shows the viability of RH30 rhabdomyosarcoma cells when treated with IPM•(LYS)$_2$ at various concentrations either once a day or three times a day.
Figure 9B:
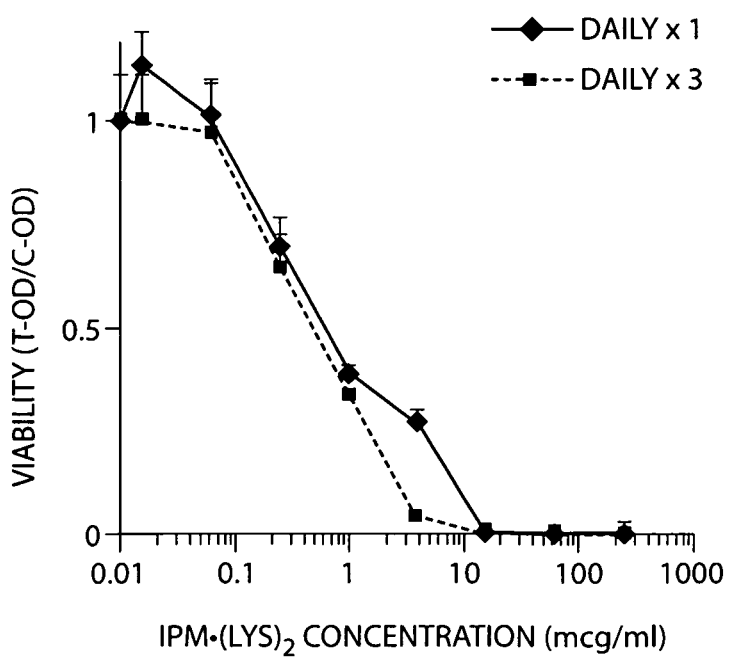
FIG. 9b shows the viability of OS229 osteosarcoma cells when treated with IPM•(LYS)$_2$ at various concentrations either once a day or three times a day.

The tumor cell lines used included RD and RH30 rhabdomyosarcoma lines (American Type Culture Collection, Manassas, Va.), Saos-2 osteosarcoma line, SKPNDW and SKES1 Ewing's sarcoma lines, and HSSYII and SYOI synovial sarcoma lines. The cells were grown in monolayer at 37° C., 5% $CO_2$ in media of MEM (Saos-2, SYO-1, HSSY-II), DME (SK-PN-DW, RD), or RPMI (RH30) supplemented with 10% fetal bovine serum (Invitrogen, Carlsbad, Calif.), 0.5% penicillin/streptomycin (Invitrogen, Carlsbad, Calif.), and 1% glutamine (Invitrogen, Carlsbad, Calif.). The results are shown below (FIGS. 8 and 9).

| Cell Line | Histology | Daily × 3 $IC_{50}$ | Daily × 1 $IC_{50}$ |
|---|---|---|---|
| SK-PN-DW | Ewing's Sarcoma | ≤0.5 µg/mL | ≤5.0 µg/mL |
| SK-ES-1 | Ewing's Sarcoma | ≤0.5 µg/mL | ≤5.0 µg/mL |
| RH30 | Alveolar Rhabdomyosarcoma | ≤1.0 µg/mL | ≤1.0 µg/mL |
| RD | Embryonal Rhabdomyosarcoma | ≤5.0 µg/mL | ≤1.0 µg/mL |
| SYO-1 | Synovial Sarcoma | ≤1.0 µg/mL | ≤1.0 µg/mL |
| HSSY-II | Synovial Sarcoma | ≤0.5 µg/mL | ≤0.5 µg/mL |
| SaOS | Osteosarcoma | ≤5.0 µg/mL | ≤5.0 µg/mL |
| OS222 | Osteosarcoma | ≤5.0 µg/mL | ≤10.0 µg/mL |
| OS229 | Osteosarcoma | ≤0.5 µg/mL | ≤0.5 µg/mL |
| OS230 | Osteosarcoma | ≤5.0 µg/mL | ≤5.0 µg/mL |

Figure 10:
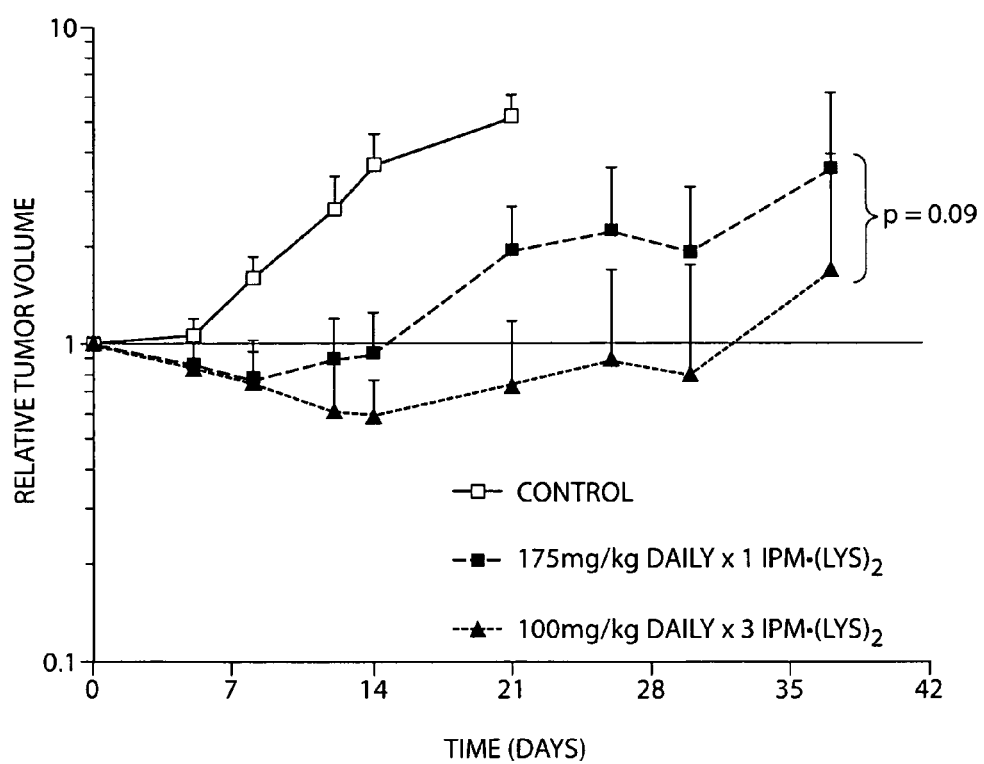
FIG. 10 shows that administration at the maximum tolerated dose (MTD) in the cyclophosphamide-resistant OS31 osteosarcoma cell line implanted in CB 17 female scid*/* mice for each of three dose schedules (control, 175 mg/kg daily×1, or 100 mg/kg daily×3), IPM•(LYS)$_2$ results in significant tumor growth delay.
Figure 11A:
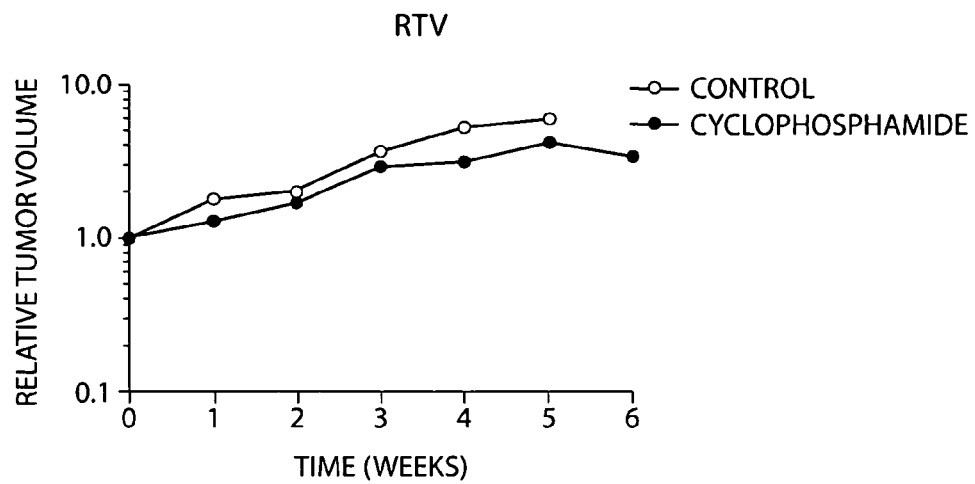
FIG. 11a shows cyclophosphamide resistance in OS31 osteosarcoma cells implanted in CB17 female scid*/* mice in terms of the relative tumor volume, where treatment comprises administration of cyclophosphamide as compared to the control.
Figure 11B:
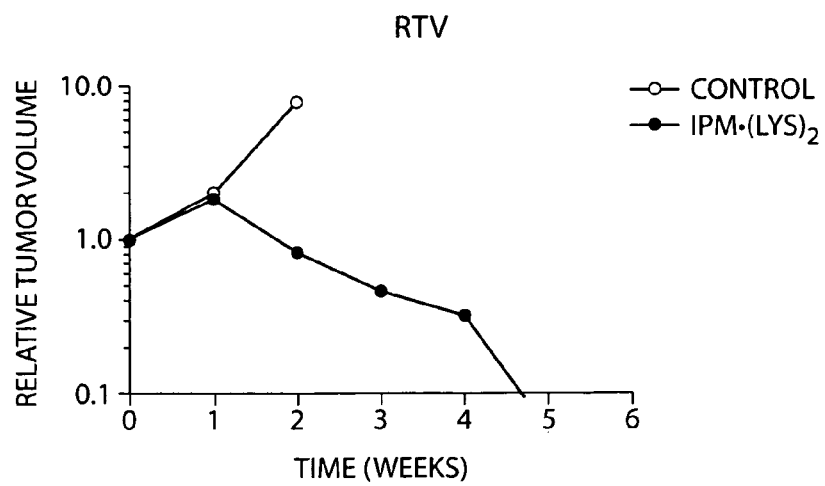
FIG. 11b shows cyclophosphamide resistance in OS33 osteosarcoma cells implanted in CB17 female scid*/* mice in terms of the relative tumor volume, where treatment comprises administration of IPM•(LYS)$_2$ as compared to the control.
Figure 12:
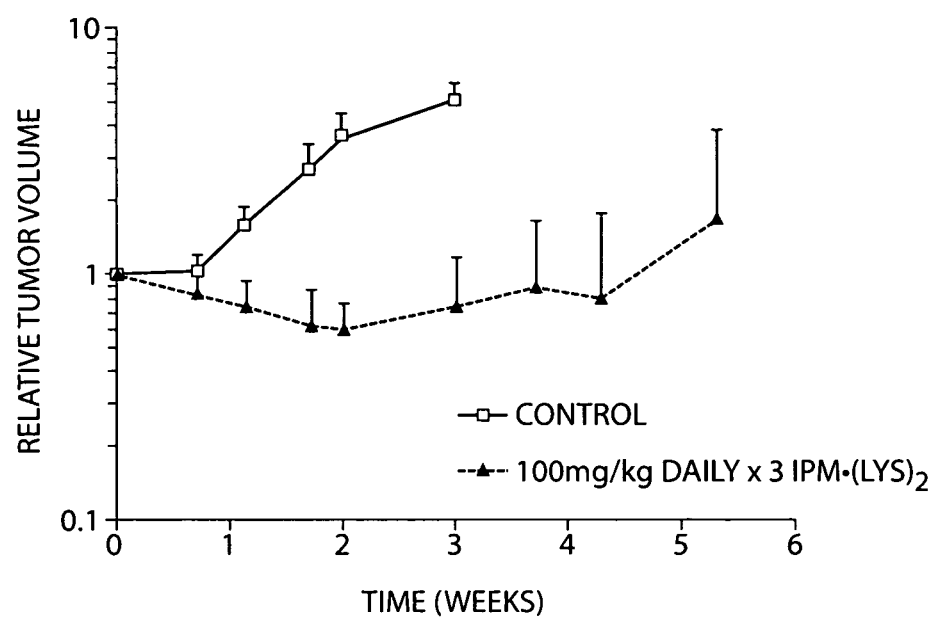
FIG. 12 shows the activity of IPM•(LYS)$_2$ in terms of relative tumor volume in the treatment of cyclophosphamide resistant OS31 osteosarcoma cells implanted in CB17 female scid*/* mice (100 mg/kg daily×3 compared to control).

Resistance to cyclophosphamide (CPA) and ifosfamide (IFOS) is a major obstacle to overcome in cancer treatment. Mice with xenografts of CPA-resistant human sarcoma cells had a more than 5-fold reduction in sarcoma growth when treated with IPM•(LYS)$_2$; CPA therapy had no effect (FIGS. 10 to 12).

Human Clinical Trials

The safety and dose-ranging phase I studies utilized IPM•(LYS)$_2$ administered daily for three consecutive days each four weeks (1 cycle). The results demonstrated evidence of clinical activity in sarcoma (2/11 subjects including at least one who had failed IFOS therapy) and mesothelioma (1 subject with extended stable disease). The maximum tolerated dose (MTD) of IPM•(LYS)$_2$ on this schedule was 400 mg/m$^2$/d. There was little bone marrow toxicity and no hemorrhagic cystitis (bladder toxicity) or CNS toxicity. The dose limiting toxicity was characterized by electrolyte imbalances. This MTD is comparable to IFOS doses of greater than 25 g/m$^2$ and this dose achieves serum levels that are 25-fold higher than doses that kill 50% of human sarcoma cell lines.

Example 6

Materials and Methods

Animal Care Five-to-six weeks-old male CD2F1 mice were purchased from Frederick Cancer Research and Development Center (Frederick, Md.).

Tumor Model: Mice were implanted ip with one million cells of the P388 murine leukemia using a 23-gauge needle. The P388 tumor line was maintained as an in vivo passage. The day of tumor implantation was designated as day 0, with treatment beginning on day 1 following tumor implantation. A sufficient number of mice were implanted so that animals with body weights in a range as narrow as possible were selected for the trial.

Drug Formulation: IPM•(LYS)$_2$, supplied in pre-weighed vials of 100 mg, was formulated in saline on the first day of treatment (day 1) at a concentration of 70 mg/mL. A portion of this solution was then diluted to the lower dosing concentrations of 46.65, 23.35, 14, 9.35, 4.65, and 2.8 mg/mL. On subsequent days of treatment, IPM•(LYS)$_2$ was formulated at 14 mg/mL and a portion of that solution was then diluted to the lower dosing concentrations. All injections were administered on the basis of exact body weight with the injection volume being 0.2 mL/10 g body weight.

Drug Treatment: The study consisted of eight treatment groups of eight mice per group and two vehicle-treated control groups with ten mice for a total of 84 mice on the first day of treatment. IPM•(LYS)$_2$ was administered as a single injection on day 1 (q1d×1) at dosages of 1400, 933, and 467 mg/kg given po and at a dosage of 280 mg/kg given ip. IPM•(LYS)$_2$ was also administered daily for five consecutive days (q1d×5) at dosages of 280, 187, and 93 mg/kg/dose given po and at a dosage of 56 mg/kg/dose given ip. One control group was treated with saline administered po as a single injection on day 1. The second control group was treated with saline administered po on a q1d×5 treatment schedule.

Study Duration: The study was terminated 61 days after tumor implantation. Any animal that became moribund was euthanized prior to study termination.

Parameters Evaluated: Number of nonspecific deaths, median days of death, and the increase in lifespan based on the median day of death and expressed as a percentage (% ILS); median survival time and the % ILS calculated based on the median survival time.

Statistical Analysis: The individual animals' survival time was used as the endpoint in a life tables analysis (stratified Kaplan-Meier estimation followed by the Mantel-Haenszel log-rank test) in order to statistically compare the survival data between groups. A life tables analysis allows one to compare the survival data between the groups using the animals that did not reach the endpoint by excluding them.

Results

The median day of death in both of the vehicle-treated control groups was 11.0, with deaths occurring between days 10 and 14. Ascites was present in all animals.

IPM•(LYS)$_2$, administered po as a single treatment given on day 1, was toxic to the mice at dosages of 1400 and 933 mg/kg. In the group receiving treatment with the dosage of 1400 mg/kg, one animal died and four animals were euthanized due to moribundity on day 5, two animals were euthanized on day 6, and the last animal died on day 10. In the group receiving treatment with the dosage of 933 mg/kg, six animals were euthanized on day 5 due to moribundity and the remaining two animals in the group died on day 9. Necropsy indicated no presence of tumor in these two treatment groups. Prior to death or euthanasia of the animals, significant weight losses of 24% and 22% were observed in groups receiving IPM•(LYS)$_2$ at dosages of 1400 and 933 mg/kg, respectively. IPM•(LYS)$_2$ administered at a dosage of 467 mg/kg as a single po treatment was better tolerated; however, two animals were euthanized on day 8 due to moribundity. The maximum loss in average body weight for this group was 8%. The remaining six animals in the group died between days 11 and 15 and were determined to have ascites present upon necropsy. The ILS for this treatment group was 9% whether the calculation was based on median day of death or median survival time. Statistical comparison of the survival data for this group with that of the vehicle-treated control group (group 1, treated q1d×1) indicated that the difference was not significant.

IPM•(LYS)$_2$, administered ip at a dosage of 280 mg/kg as a single injection was tolerated without deaths and with a minimal loss in mean body weight (4%, 1 g). The median day of death for this group was 34.5 with an ILS of 214%. The median survival time was 38.0 days with an ILS of 245%. Additionally, two animals survived until study termination on day 61. Necropsy indicated no tumor present. Statistical analysis of the survival data for this treatment group and the vehicle-treated control group (group 1, treated q1d×1) indicated the difference was significant.

IPM•(LYS)$_2$, administered po at dosages of 280, 187, and 93 mg/kg/dose on a q1d×5 treatment schedule, was tolerated without treatment-related deaths. A minimal loss in mean body weight (4%, 1 g) was observed in the group receiving IPM•(LYS)$_2$ at a dosage of 280 mg/kg/dose. No weight loss was observed for the two lower dosage groups. Median days of death and median survival times were 17.0, 17.0, and 15.0 days with ILS values of 55%, 55%, and 36% for the dosages of 280, 187, and 93 mg/kg/dose, respectively. Statistical comparison of the survival data for each of these three groups with survival data for the vehicle-treated control (group 6, treated q1d×5) indicated the increase in lifespan for each group was statistically significant.

IPM•(LYS)$_2$, given ip at a dosage of 56 mg/kg/dose on a q1d×5 injection schedule, was quite effective against the P388/0 leukemia with a median day of death of 28.5 The first death occurred on day 24 and the last death on day 33, with four of the eight animals in the group surviving until the time of the study termination on day 61. The ILS value calculated based on median day of death was 159%. The median survival time for this treatment group was >47.0 days with a calculated ILS value of 327%. This treatment regimen was well-tolerated with no treatment-related deaths and a 4% (1 g) loss in mean body weight. When the survival data for this group was statistically compared to that of the vehicle-treated control group (group 6, treated q1d×5) the difference was found to be significant.

Summary of Statistical Analysis

| Group Pairs | p value |
| --- | --- |
| 1 vs. 4 | 0.192 |
| 1 vs. 5 | 0.000 |
| 4. vs. 5 | 0.000 |
| 6 vs. 7 | 0.000 |
| 6 vs. 8 | 0.000 |
| 6 vs. 9 | 0.000 |
| 6 vs. 10 | 0.000 |
| 7 vs. 10 | 0.000 |

Conclusions

IPM•(LYS)$_2$ was toxic to the mice when administered po as a single treatment at dosages of 1400 and 933 mg/kg. A single treatment with the dosage of 467 mg/kg administered po was tolerated but elicited only a minimal increase in lifespan that was not statistically significant. IPM•(LYS)$_2$, administered as a single ip injection at a dosage of 280 mg/kg, was quite effective and resulted in two 61-day survivors and a significant increase in lifespan.

IPM•(LYS)$_2$, administered po on a q1d×5 schedule at dosages of 280, 187, and 93, was much better tolerated and more effective against the P388/0 leukemia than the single treatments with higher dosages. Treatment with all three dosages given po q1d×5 produced statistically significant increases in lifespan. When administered ip on a q1d×5 treatment schedule at a dosage of 56 mg/kg/dose, IPM•(LYS)$_2$ elicited significant increases in lifespan with four of eight animals in the group surviving until study termination on day 61.

Example 7

Materials and Methods

Animal Care Five-weeks-old female athymic NCr-nu/nu mice were purchased from Taconic Farms (Germantown, N.Y.).

Tumor Model: 30 to 40 mg fragments of MX-1 human mammary tumors maintained in an in vivo passage were implanted sc in mice in the mammary fat pad using a 12-gauge trocar needle and allowed to grow. The day of tumor implantation was designated as day 0. Tumors were allowed to reach 138-245 mg in weight (138-245 mm in size) before the start of treatment. A sufficient number of mice were implanted so that tumors in a weight range as narrow as possible were selected for the trial on the day of treatment initiation (day 10 after tumor implantation). Those animals selected with tumors in the proper size range were assigned to the various treatment groups so that the median tumor weights on the first day of treatment were as close to each other as possible (172-197 mg).

Drug Formulation: IPM•Tris (205 mg of IPM/vial) which may be prepared as described in Example 1, and IPM were both formulated in saline on the first day of treatment (day 10) at a concentration of 6.0 mg/mL and then diluted with saline to the lower dosing concentrations of 4.05, 1.8, and 1.2 mg/mL. IPM•(LYS)$_2$ (100 mg IPM-Lysine/vial) was formulated in saline on the first day of treatment at a concentration of 14 mg/mL and then diluted with saline to the lower dosing concentrations of 9.35, 4.2 and 2.8 mg/mL. Each concentration was then aliquoted for daily use, frozen, stored at −20° C., and thawed for daily use. All injections were administered on the basis of exact body weight with the injection volume being 0.2 mL/10 g body weight.

Drug Treatment: The experiment consisted of 12 treatment groups of eight mice per group and two vehicle-treated control groups with ten mice each for a total of 116 mice on the first day of treatment. All agents (and vehicle) were administered daily for five consecutive days (q1d×5). IPM•Tris and IPM were both administered ip at dosages of 36 and 24 mg/kg/dose and po at dosages of 120 and 81 mg/kg/dose. IPM•(LYS)$_2$ was administered ip at dosages of 84 and 56 mg/kg/dose and po at dosages of 280 and 187 mg/kg/dose. The control groups were treated either ip or po with the vehicle (saline).

Tumor Measurements and Body Weights: The sc tumors were measured and the animals were weighed twice weekly starting with the first day of treatment. Tumor volume was determined by caliper measurements (mm) and using the formula for an ellipsoid sphere:

$$L \times W^2/2 = mm^3,$$

where L and W refer to the larger and smaller perpendicular dimensions collected at each measurement. This formula is also used to calculate tumor weight, assuming unit density (1 mm$^3$=1 mg).

Study Duration: The study was terminated 50 days after tumor implantation. Any animal that became moribund or whose tumor became ulcerated or reached 4,000 mg was euthanized prior to study termination.

Parameters Evaluated: Number of nonspecific deaths, number of partial and complete tumor regressions, number of tumor-free survivors, and the individual animals' times to reach two tumor mass doublings were determined. The median time to reach two tumor mass doublings in the treatment groups (T) and control group (C) was used in the calculation of the overall delay in the growth of the median tumor (T-C).

Statistical Analysis: The individual animal's time to reach two tumor mass doublings was used as the endpoint in a Student's t-test/Mann Whitney rank sum test or life tables analysis in order to compare statistically the growth data between groups. A life tables analysis (stratified Kaplan-Meier estimation followed by the Mantel-Haenszel log-rank test) allows one to compare the growth data between groups using the animals whose tumors did not reach the evaluation point by excluding them.

Results

Tumors in both vehicle-treated control groups grew well in all 10 mice. The median tumor reached two tumor mass doublings in 7.4 and 7.2 days, respectively, for the ip-treated and po-treated groups. There was no loss in mean body weight for these two groups during the study.

Intraperitoneal administration of IPM•Tris at dosages of 36 and 24 mg/kg/dose elicited tumor growth delays (T-C) of 10.2 and 7.7 days, respectively. The higher dosage had one tumor-free survivor. Both dosages were tolerated with maximum losses in mean body weight of 10% (2 g) and 0% for dosages of 36 and 24 mg/kg/dose, respectively. Intraperitoneal administration of IPM at dosages of 36 and 24 mg/kg/dose elicited tumor growth delays of 5.2 and 2.6 days, respectively. Both dosages were tolerated with maximum losses in mean body weight of 0% and 5% (1 g) for dosages of 36 and 24 mg/kg/dose, respectively. The times to reach two tumor mass doublings for IPM were statistically less than that for the corresponding dosage of IPM•Tris (p=0.000 for the dosage of 36 mg/kg/dose; p=0.021 for the dosage of 24 mg/kg/dose). Intraperitoneal administration of IPM•(LYS)$_2$ at dosages of 84 and 56 mg/kg/dose, which correspond to IPM dosages of 36 and 24 mg/kg/dose, elicited tumor growth delays of 24.3 and 9.0 days, respectively. The higher dosage of IPM•(LYS)$_2$ was toxic—two mice dead on day 20 and two euthanized because of morbundity or excessive loss in body weight. The lower dosage of IPM•(LYS)$_2$ was tolerated with a maximum loss in mean body weight of 15% (3 g). The tolerated IPM•(LYS)$_2$ dosage exhibited comparable activity to that for IPM•Tris at a corresponding dosage of 24 mg/kg/dose (p=0.766) and superior activity to that for IPM at a corresponding dosage of 24 mg/kg/dose (p=0.0047).

Oral administration of IPM•Tris at dosages of 120 and 81 mg/kg/dose elicited tumor growth delays of 8.7 and 9.0 days, respectively. The higher dosage of IPM•Tris elicited a maximum loss in mean body weight of 15% (3 g) with one mouse being euthanized because of a body weight less than 14 g. The lower dosage was tolerated with a maximum loss in mean body weight of 10% (2 g). Oral administration of IPM at dosages of 120 and 81 mg/kg/dose elicited tumor growth delays of 4.6 and 4.0 days, respectively. Both dosages were tolerated with a maximum loss in mean body weight of 5% (1 g). The times to reach two tumor mass doublings were not statistically different from the times for the corresponding dosage of IPM•Tris (p=0.1174 for the dosage of 120 mg/kg/dose; p=0.1152 for the dosage of 81 mg/kg/dose). Oral administration of IPM•(LYS)$_2$ at dosages of 280 and 187 mg/kg/dose, which correspond to IPM dosages of 120 and 81 mg/kg/dose, elicited tumor growth delays of 5.0 and 3.5 days, respectively. Both dosages were tolerated with maximum losses in mean body weight of 5% (1 g) and 0%. The higher dosage of IPM•(LYS)$_2$ exhibited comparable activity to that for both IPM•Tris and IPM at a corresponding dosage of 120 mg/kg/dose (p=0.1000 and p=0.9143, respectively). The lower dosage of IPM•(LYS)$_2$ exhibited inferior activity to that for IPM•Tris at a corresponding dosage of 81 mg/kg/dose (p=0.0290) and comparable activity to that for IPM at a corresponding dosage of 81 mg/kg/dose (p=0.3073).

Summary of Table of Statistical Analysis

| Group Pairs | p Value |
|---|---|
| 2 vs 4 | 0.000[1] |
| 3 vs 5 | 0.021[1] |
| 3 vs 7 | 0.766[1] |
| 5 vs 7 | 0.0047[2] |
| 9 vs 11 | 0.1174[3] |
| 9 vs 13 | 0.1000[3] |
| 11 vs 13 | 0.9143[3] |
| 10 vs 12 | 0.1152[3] |
| 10 vs 14 | 0.0290[3] |
| 12 vs 14 | 0.3073[3] |

[1]Life tables analysis
[2]Mann-Whitney rank sum test
[3]Student's t-test

Figure 13:
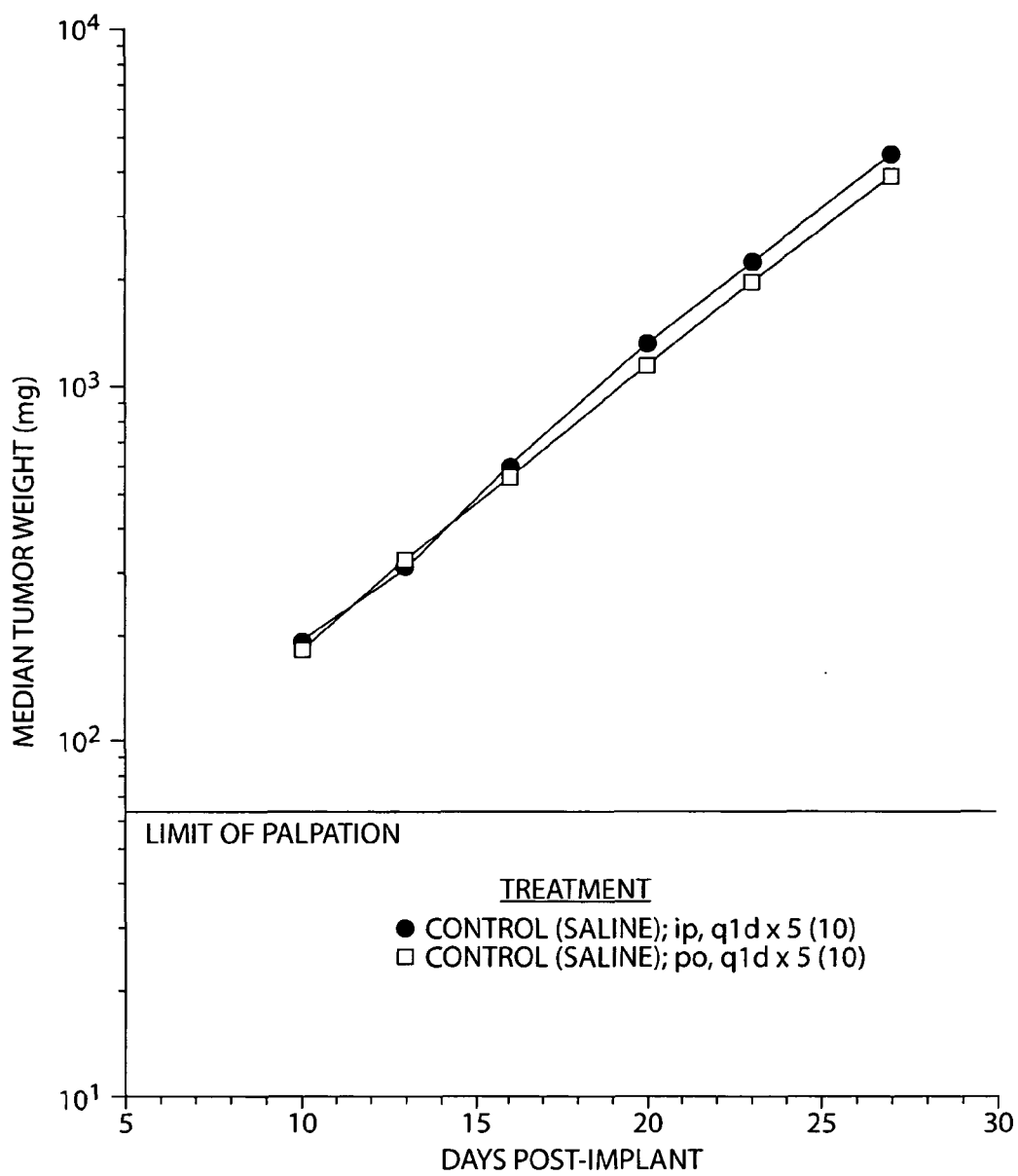
FIG. 13 shows the response of SC MX-1 mammary tumors to IP and oral treatment with saline with a dose of q1d×5.
Figure 14:
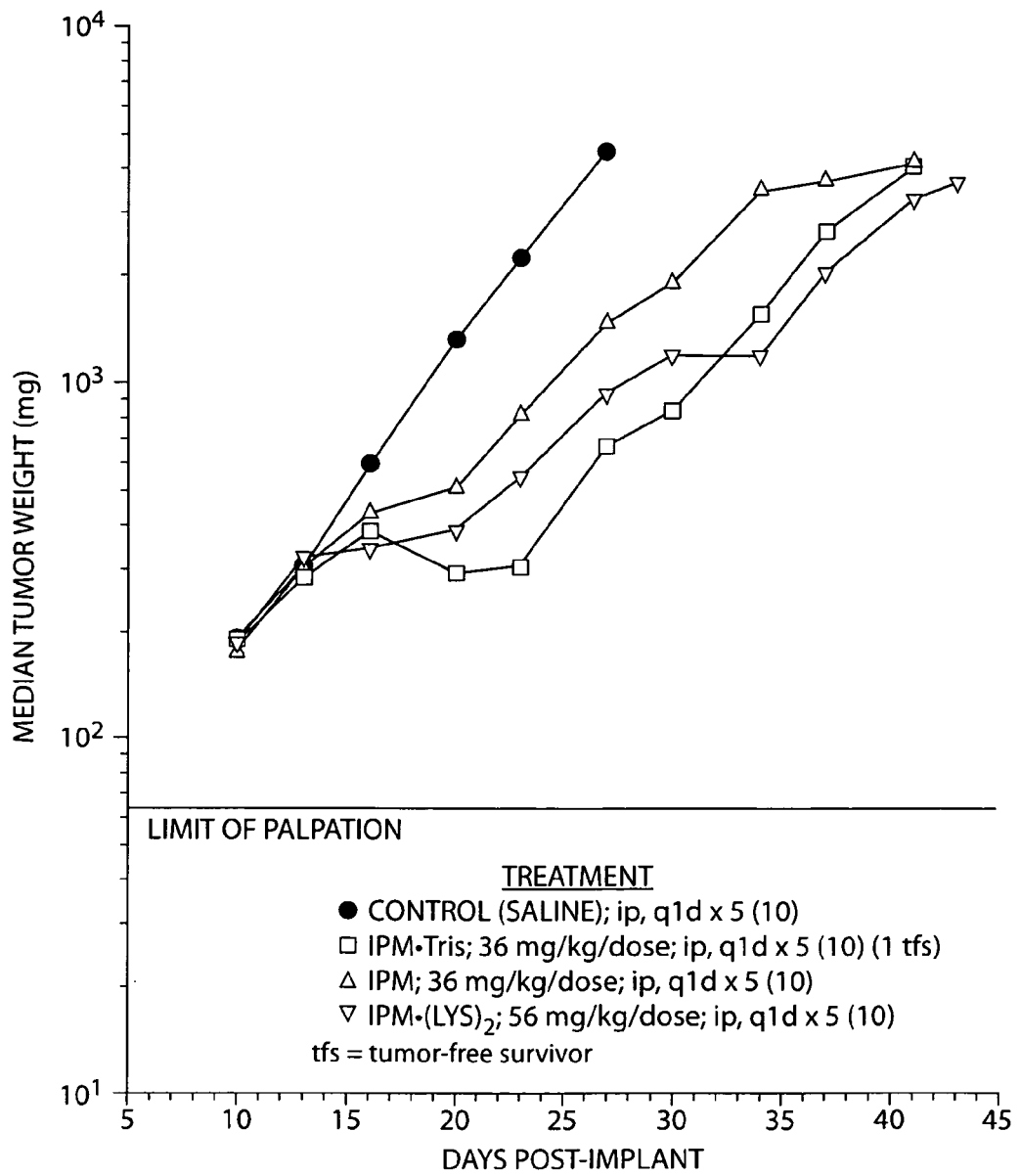
FIG. 14 shows the response of SC MX-1 mammary tumors to IP treatment with IPM•Tris, IPM and IPM•(LYS)$_2$ with a dose of q1d×5.
Figure 15:
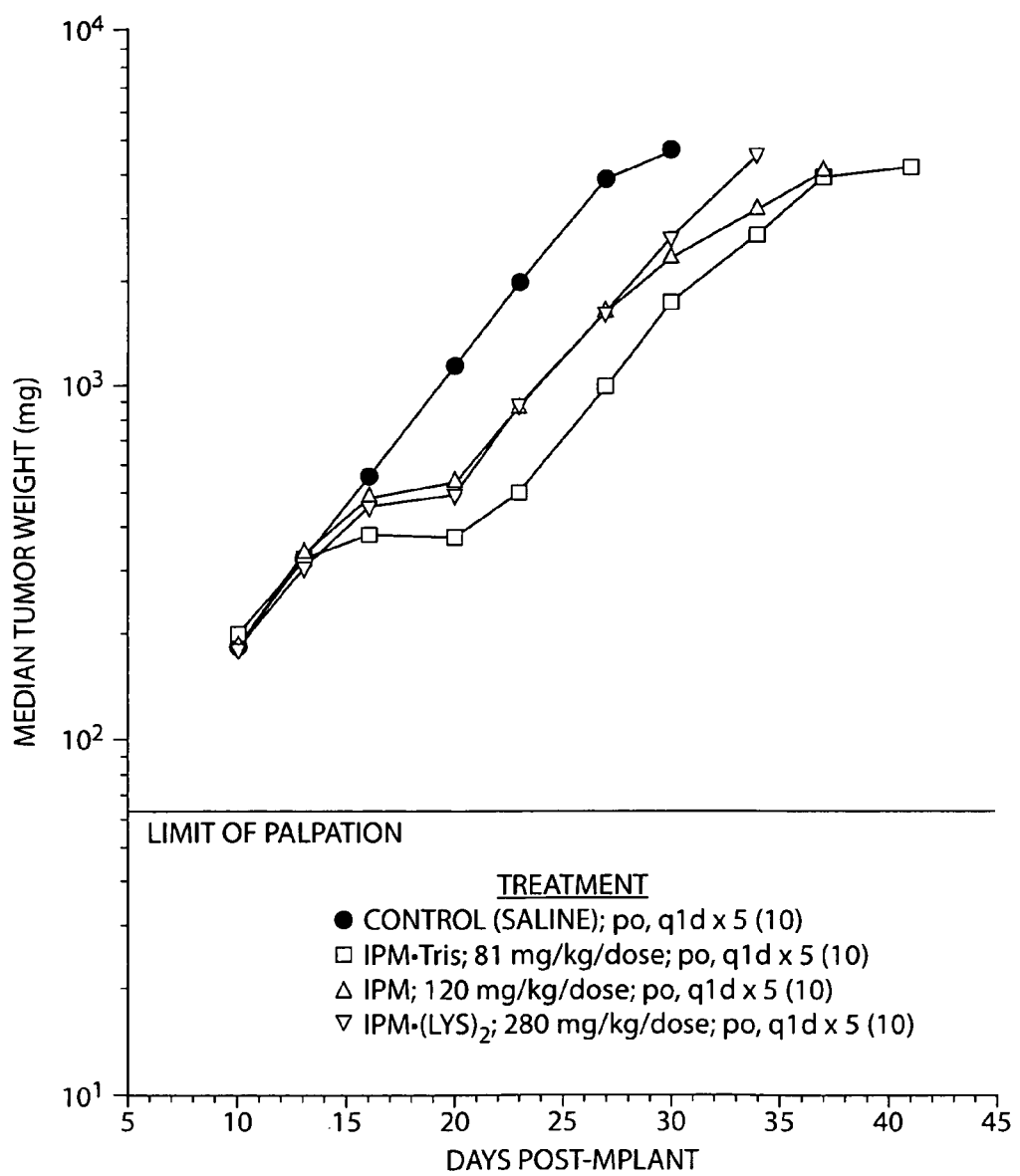
FIG. 15 shows the response of SC MX-1 mammary tumors to oral treatment with IPM•Tris, IPM and IPM•(LYS)$_2$ with a dose of q1d×5.

The response of the MX-1 human mammary tumor xenografts to treatment with (1) vehicle—ip and po, (2) ip IPM•Tris, IPM, and IPM•(LYS)$_2$, and (3) po IPM•Tris, IPM, and IPM•(LYS)$_2$ is shown in FIGS. 13, 14, and 15, respectively.

Conclusion

For ip administration of equivalent IPM dosages the antitumor activity of IPM•Tris was superior to that for IPM (both dosages) and comparable to that for IPM•(LYS)$_2$ (both dosages). For po administration of equivalent IPM dosages, the antitumor activity of IPM•Tris was comparable to that for IPM (both dosages), comparable to that for IPM•(LYS)$_2$ at the higher dosage, and superior to that for IPM•(LYS)$_2$ at the lower dosage.

Example 8

Materials and Methods

Animal Care Five-weeks-old female athymic NCr-nu/nu mice were purchased from Harlan (Prattville, Ala.).

Tumor Model: Thirty-to-forty mg fragments of MX-1 human mammary tumor maintained in an in vivo passage were implanted sc in mice in the mammary fat pad using a 12-gauge trocar needle and allowed to grow. The day of tumor implantation was designated as day 0. Tumors were allowed to reach 113-245 mg in weight (113-245 mm$^3$ in size) before the start of treatment. A sufficient number of mice were implanted so that tumors in a weight range as narrow as possible were selected for the trial on the day of treatment initiation (day 6 after tumor implantation). Those animals selected with tumors in the proper size range were assigned to the various treatment groups so that the median tumor weights on the first day of treatment were as close to each other as possible (144-162 mg).

Drug Formulation: IPM•Tris (205 mg of IPM/vial, Cardinal Health) which may be prepared as described in Example 1, was formulated in saline on each day of treatment at a concentration of 13.5 mg/mL and then diluted with saline to the lower dosing concentrations of 9, 6, 4.05, 2.7, 1.8, and 1.2 mg/mL. IPM (Eagle-Picher Pharmaceutical Service) was formulated in saline on each day of treatment at a concentration of 6.0 mg/mL and then diluted with saline to the lower dosing concentrations of 4.05, 1.8, and 1.2 mg/mL. IPM•(LYS)$_2$ (100 mg IPM-Lysine/vial, University of Iowa) was formulated in saline on the each day of treatment at a concentration of 14 mg/mL and then diluted with saline to the lower dosing concentrations of 9.35, 4.2, and 2.8 mg/mL. All dosing solutions were kept on ice after formulation and were administered within 30 min. All injections were administered on the basis of exact body weight with the injection volume being 0.2 mL/10 g body weight.

Drug Treatment: The experiment consisted of 16 treatment groups of eight mice per group and two vehicle-treated control groups with ten mice each for a total of 148 mice on the first day of treatment. All agents (and vehicle) were administered daily for five consecutive days (q1d×5). IPM•Tris was administered ip at dosages of 81, 54, 36, and 24 mg/kg/dose and po at dosages of 270, 180, 120 and 81 mg/kg/dose. IPM was administered ip at dosages of 36 and 24 mg/kg/dose and po at dosages of 120 and 81 mg/kg/dose. IPM•(LYS)$_2$ was administered ip at dosages of 84 and 56 mg/kg/dose and po at dosages of 280 and 187 mg/kg/dose. The control groups were treated either ip (group no. 1) or po (group no. 10) with the vehicle (saline).

Tumor Measurements and Body Weights: The sc tumors were measured and the animals were weighed twice weekly starting with the first day of treatment. Tumor volume was determined by caliper measurements (mm) and using the formula for an ellipsoid sphere:

$$L \times W^2/2 = mm^3,$$

where L and W refer to the larger and smaller perpendicular dimensions collected at each measurement. This formula is also used to calculate tumor weight, assuming unit density (1 mm=1 mg.).

Study Duration: The study was terminated 52 days after tumor implantation. Any animal that became moribund or whose tumor became ulcerated and reached 4,000 mg was euthanized prior to study termination.

Parameters Evaluated: Number of nonspecific deaths, number of partial and complete tumor regressions, number of tumor-free survivors, and the individual animals' times to reach two tumor mass doublings were determined. The median time to reach two tumor mass doubling in the treatment groups (T) and control group (C) was used in the calculation of the overall delay in the growth of the median tumor (T-C).

Statistical Analysis: The individual animal's time to reach two tumor mass doublings was used as the endpoint in a Student's t-test/Mann Whitney rank sum test in order to compare statistically the growth data between groups.

Results

Tumors in both vehicle-treated control groups grew well in all 10 mice. The median tumor reached two tumor mass doublings in 9.2 and 8.9 days, respectively, for the ip-treated and po-treated groups. There was no loss in mean body weight for these two groups during the study.

Intraperitoneal administration of IPM•Tris at a dosage of 81 mg/kg/dose was toxic to the mice, eliciting three deaths and one euthanasia due to morbundity and a maximum loss in mean body weight of 20% (4.5 g). The lower dosages of 54, 36, and 24 mg/kg/dose were tolerated with maximum losses in mean body weight of 5% (1.2 g), 6% (1.3 g), and 1% (0.2 g), respectively. The dosages of 54, 35, and 24 mg/kg/dose elicited tumor growth delays (T-C) of 4.4, 3.3, and 0.9 days, respectively. Intraperitoneal administration of IPM at dosages of 36 and 24 mg/kg/dose elicited tumor growth delays of 1.1 and 0.3 days, respectively. Both dosages were tolerated with maximum losses in mean body weight of 8% (1.8 g) and 2% (0.4 g) for dosages of 36 and 24 mg/kg/dose, respectively. The times to reach two tumor mass doublings for IPM were statistically less than that for the highest tolerated dosages of IPM•Tris but statistically the same as the corresponding dosage of IPM•Tris (p=0.0148 for the dosage of 54 mg/kg/dose; p=0.1879 for the dosage of 36 mg/kg/dose). Intraperitoneal administration of IPM•(LYS)$_2$ at dosages of 84 and 56 mg/kg/dose, which correspond to IPM dosages of 36 and 24 mg/kg/dose, elicited tumor growth delays of 0.5 and 0.3 day, respectively. Both dosages were tolerated with maximum losses in mean body weight of 1% (0.3 g) and 0% for dosages of 36 and 24 mg/kg/dose, respectively. The times to reach two tumor mass doublings for IPM•(LYS)$_2$ were statistically less than that for the highest tolerated dosage of IPM•Tris but statistically the same as the corresponding dosage of IPM•Tris (p=0.0104 for the dosage of 54 mg/kg/dose; p=0.1578 for the dosage of 36 mg/kg/dose).

Oral administration of IPM•Tris at dosages of 270, 180, and 120 mg/kg/dose was toxic to the mice, eliciting eight deaths/euthanasia due to morbundity, seven deaths, and three deaths, respectively. The dosages of 180 and 120 mg/kg/dose elicited maximum losses in mean body weight of 23% (5.3 g) and 20% (4.7 g), respectively. The lowest dosage of 81 mg/kg/dose was tolerated with a maximum loss in mean body weight of 10% (2.2 g). The dosage of 81 mg/kg/dose elicited a tumor growth delay of 2.6 days. Oral administration of IPM at a dosage of 120 mg/kg/dose was toxic to the mice, eliciting two deaths and a maximum loss in mean body weight of 18% (3.8 g). The lower dosage of 81 mg/kg/dose was tolerated with a maximum loss in mean body weight of 9% (2 g) and elicited a tumor growth delay of 2.3 days. The times to reach two tumor mass doublings were not statistically different from the times for the corresponding dosage of IPM•Tris (p=0.2932 for the dosage of 81 mg/kg/dose). Oral administration of IPM•(LYS)$_2$ at dosages of 280 and 187 mg/kg/dose, which correspond to IPM dosages of 120 and 81 mg/kg/dose, elicited tumor growth delays of 3.9 and 4.7 days, respectively. Both dosages were tolerated with maximum losses in mean body weight of 14% (3 g) and 7% (1.6 g). The lower dosage of IPM•(LYS)$_2$ exhibited similar activity to that for IPM•Tris at a corresponding dosage of 81 mg/kg/dose (p=0.8785).

Summary Table of Statistical Analysis

| Group Pairs | p Value |
|---|---|
| 1 vs. 3 | 0.00101 |
| 1 vs. 6 | 0.02302 |
| 1 vs. 8 | 0.1456[2] |
| 3 vs. 6 | 0.0148[1] |
| 3 vs. 8 | 0.0104[1] |
| 4. vs. 6 | 0.1879[2] |
| 4 vs. 8 | 0.1578[2] |
| 10 vs. 14 | 0.0053[2] |
| 10 vs. 16 | 0.0234[1] |
| 10 vs. 17 | 0.0039[1] |
| 14 vs. 16 | 0.2932[2] |
| 14 vs. 17 | 0.7209[1] |
| 14 vs. 18 | 0.8785[1] |

[1]Mann-Whitney rank sum test
[2]Student's t-test

Figure 16:
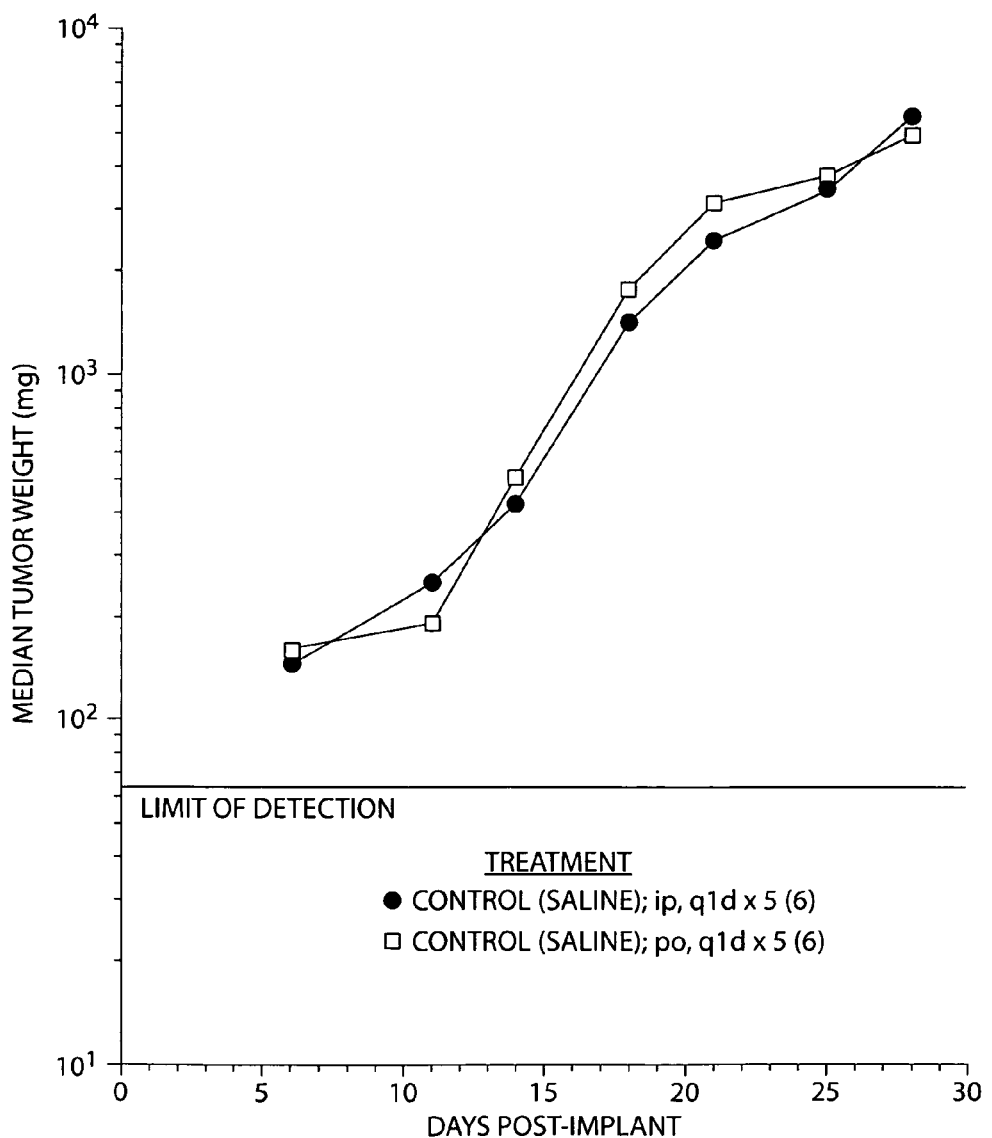
FIG. 16 shows the response of SC MX-1 mammary tumors to IP and oral treatment with saline with a dose of q1d×5.
Figure 17:
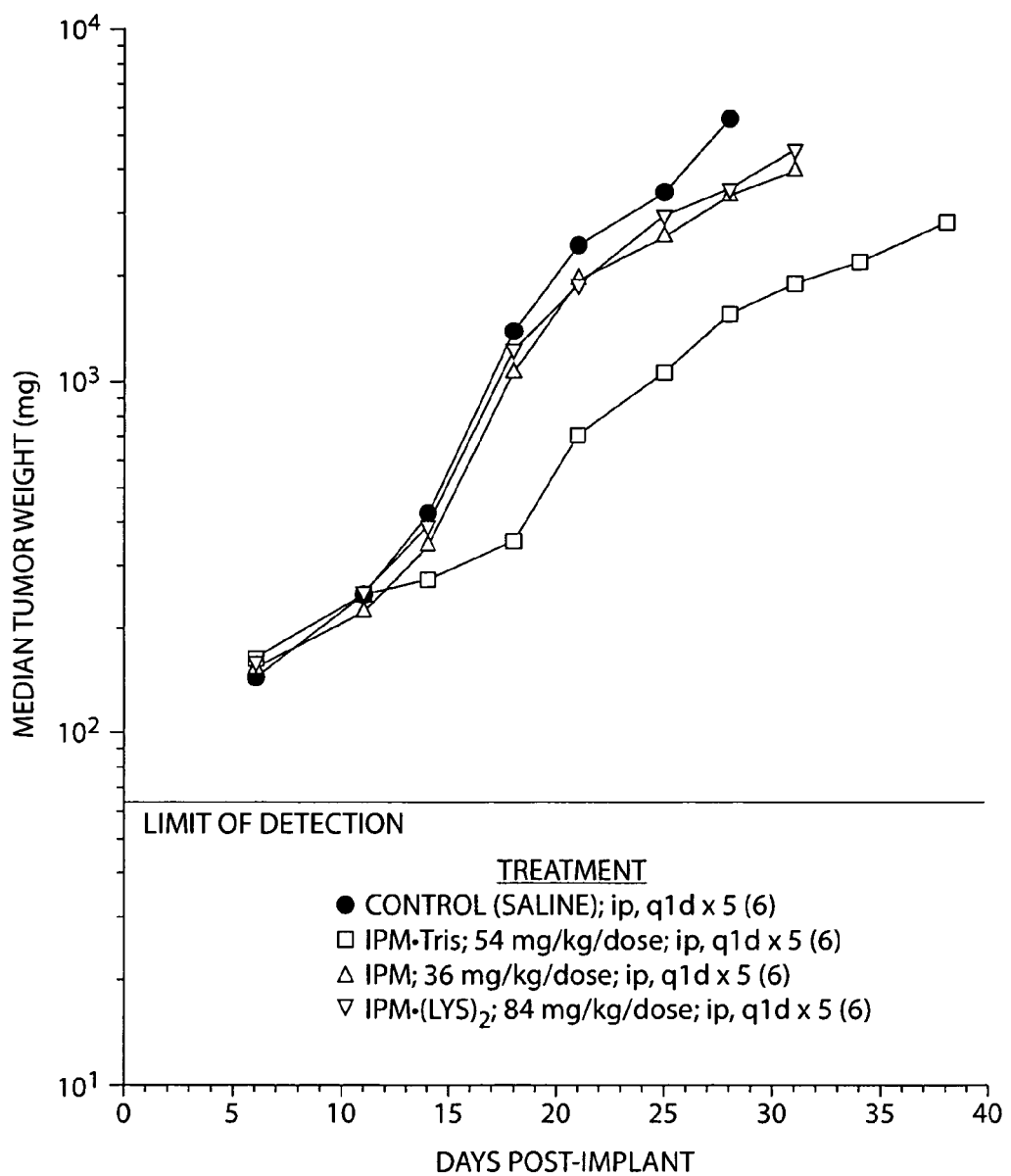
FIG. 17 shows the response of SC MX-1 mammary tumors to IP treatment with IPM•Tris, IPM and IPM•(LYS)$_2$ with a dose of q1d×5.
Figure 18:
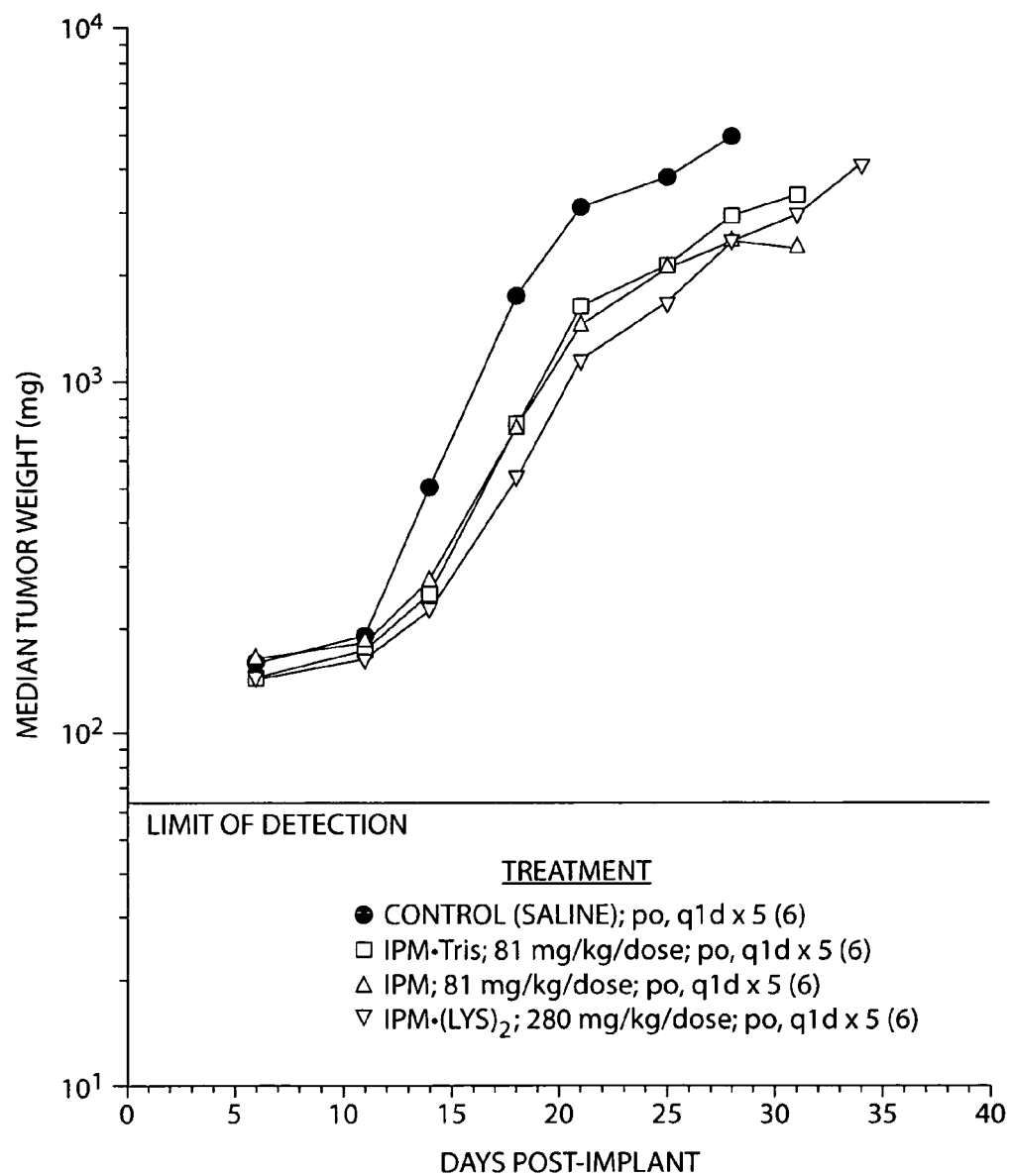
FIG. 18 shows the response of SC MX-1 mammary tumors to oral treatment with IPM•Tris, IPM and IPM•(LYS)$_2$ with a dose of q1d×5.
Figure 19:
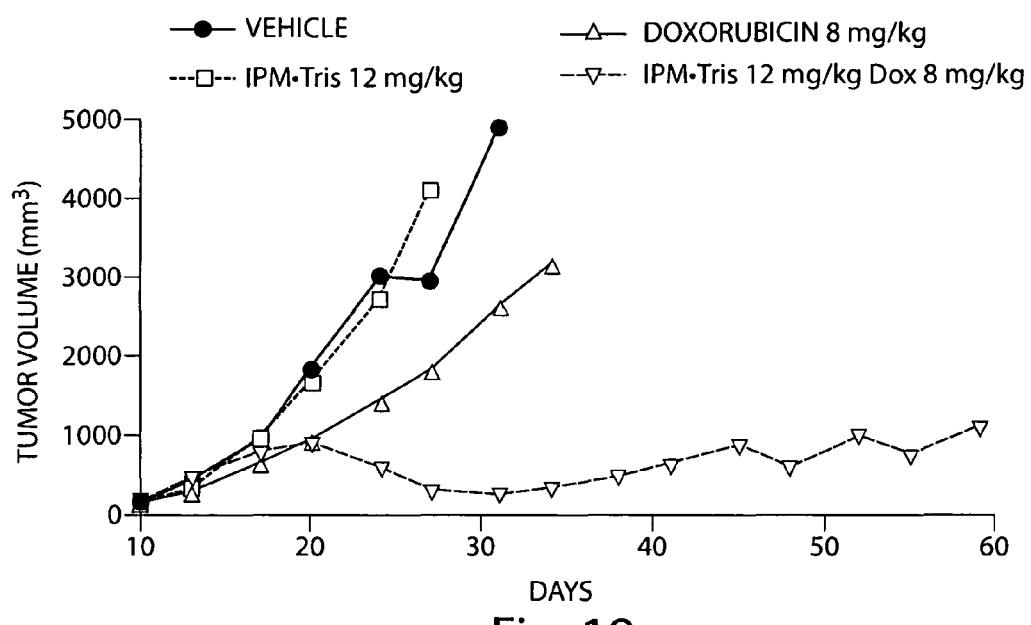
FIG. 19 shows the effect of MX-1 breast cancer tumors to treatment with IPM•Tris in combination with doxorubicin with a dose of 12 mg/kg/day IPM•Tris Q1D×5 and 8 mg/kg doxorubicin Q4D×3.
Figure 20:
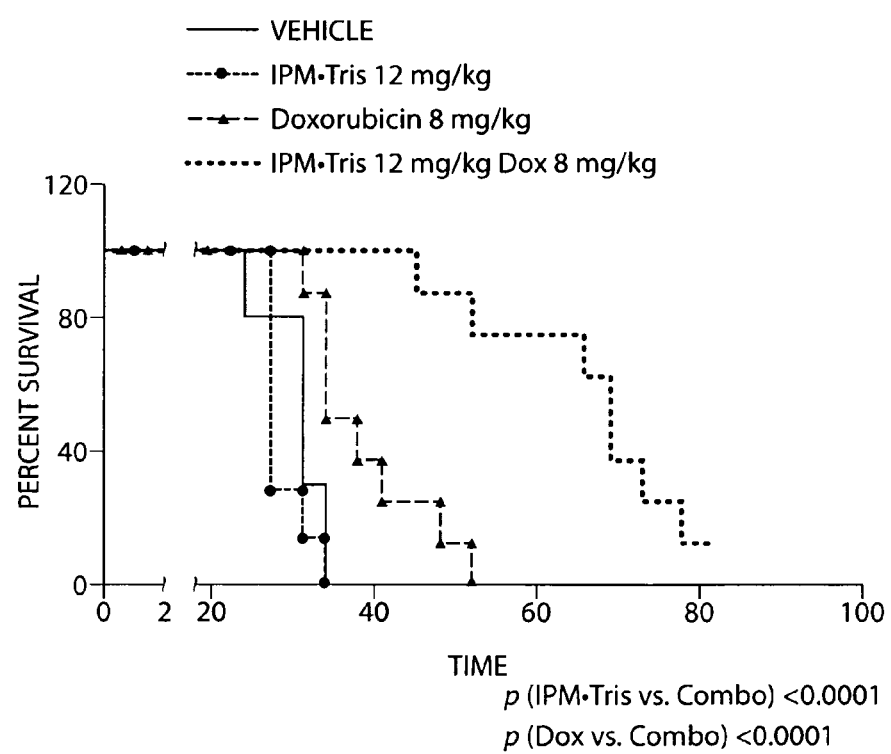
FIG. 20 shows the effect on survival of IPM•Tris in combination with doxorubicin with a dose of 12 mg/kg/day IPM•Tris Q1D×5 and 8 mg/kg doxorubicin Q4D×3.
Figure 21:
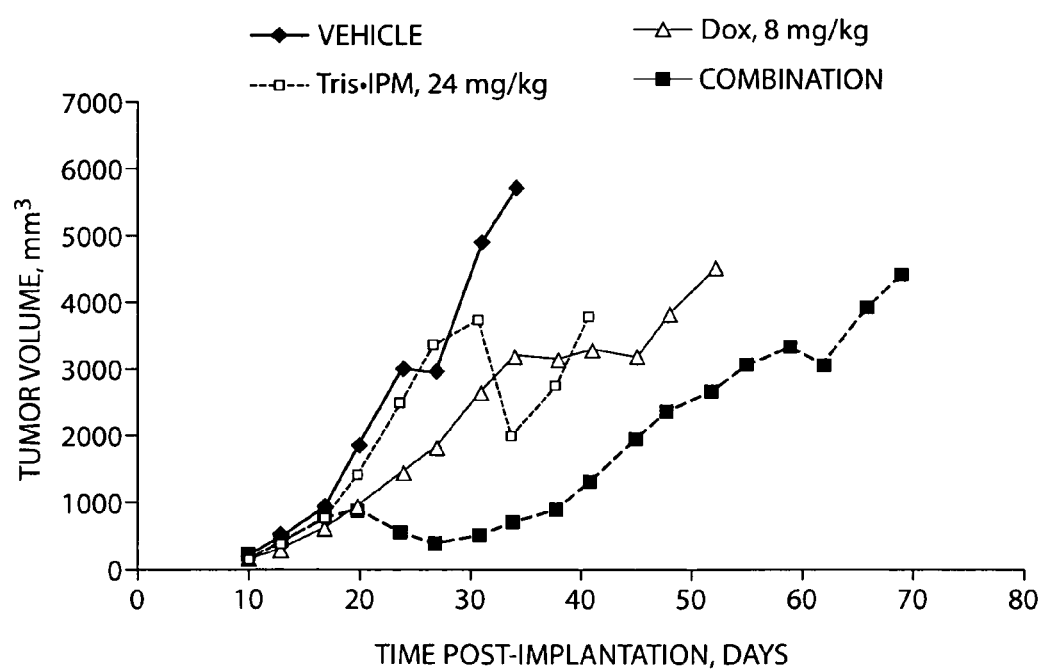
FIG. 21 shows the effect on MX-1 breast cancer tumors of treatment with IPM•Tris in combination with doxorubicin with a dose of 24 mg/kg/day IPM•Tris Q1D×5 and 8 mg/kg doxorubicin Q4D×3.
Figure 22:
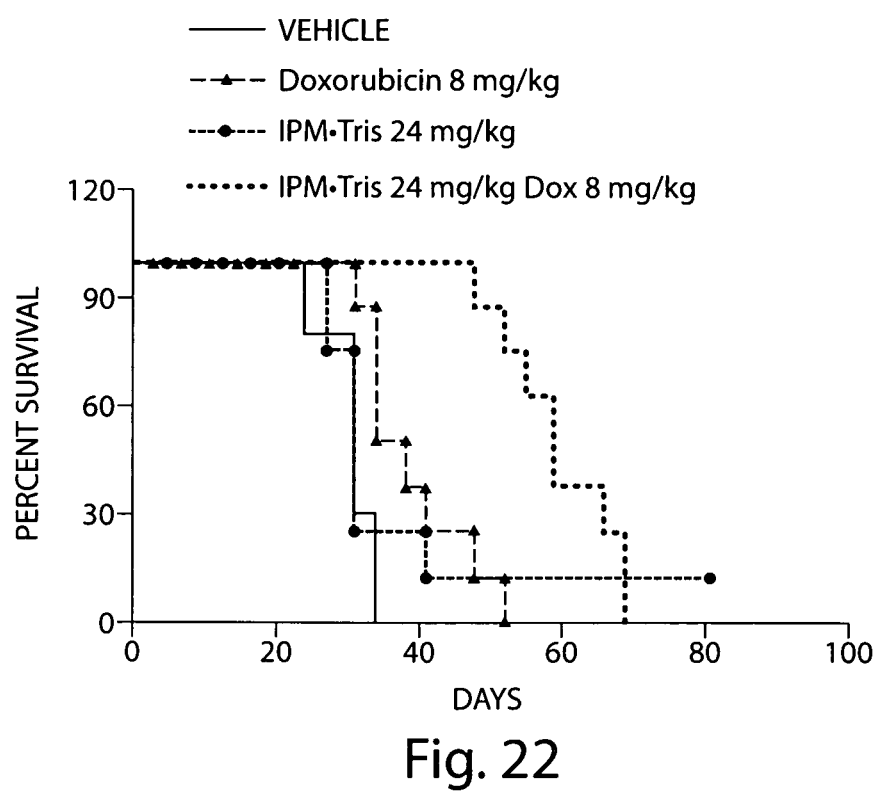
FIG. 22 shows the effect on survival of IPM•Tris in combination with doxorubicin with a dose of 24 mg/kg/day IPM•Tris Q1D×5 and 8 mg/kg doxorubicin Q4D×3.
Figure 23:
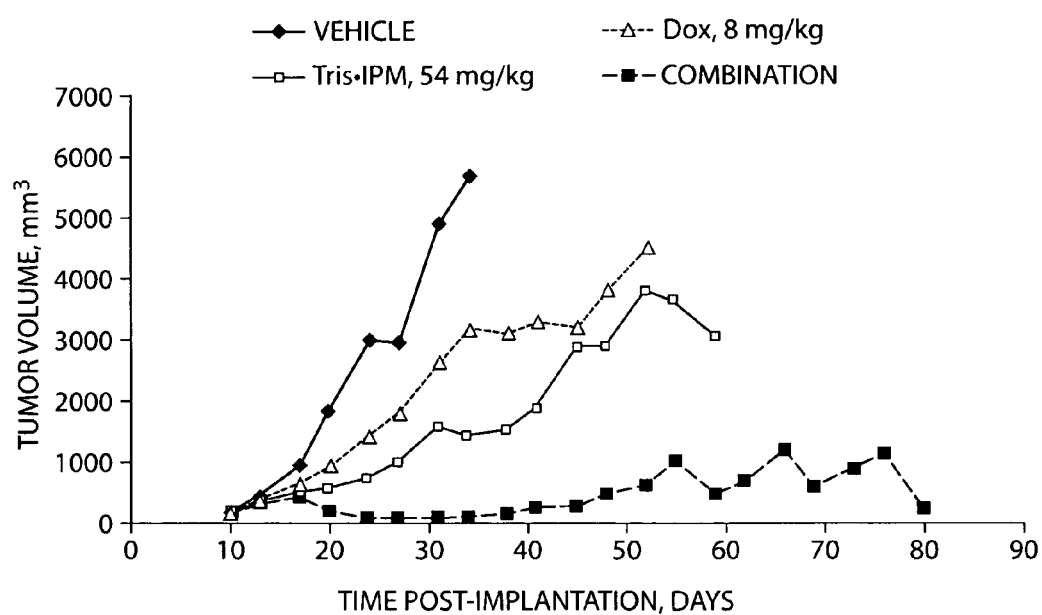
FIG. 23 shows the effect on MX-1 breast cancer tumors of treatment with IPM•Tris in combination with doxorubicin with a dose of 54 mg/kg/day IPM•Tris Q1D×5 and 8 mg/kg doxorubicin Q4D×3.
Figure 24:
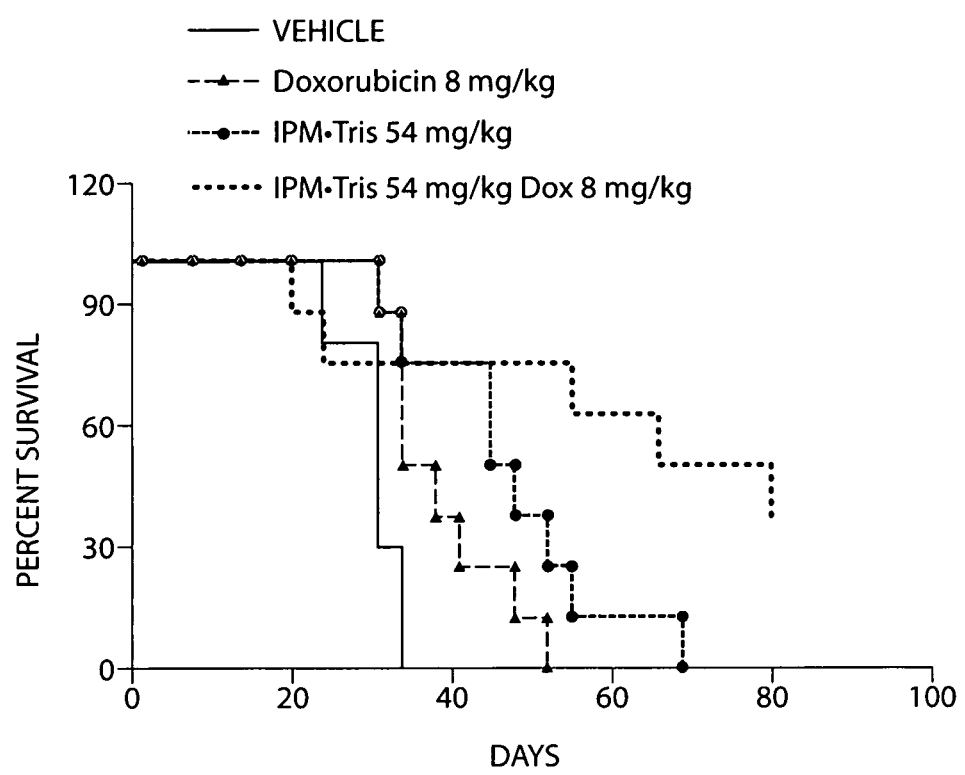
FIG. 24 shows the effect on survival of IPM•Tris in combination with doxorubicin with a dose of 54 mg/kg/day IPM•Tris Q1D×5 and 8 mg/kg doxorubicin Q4D×3.
Figure 25:
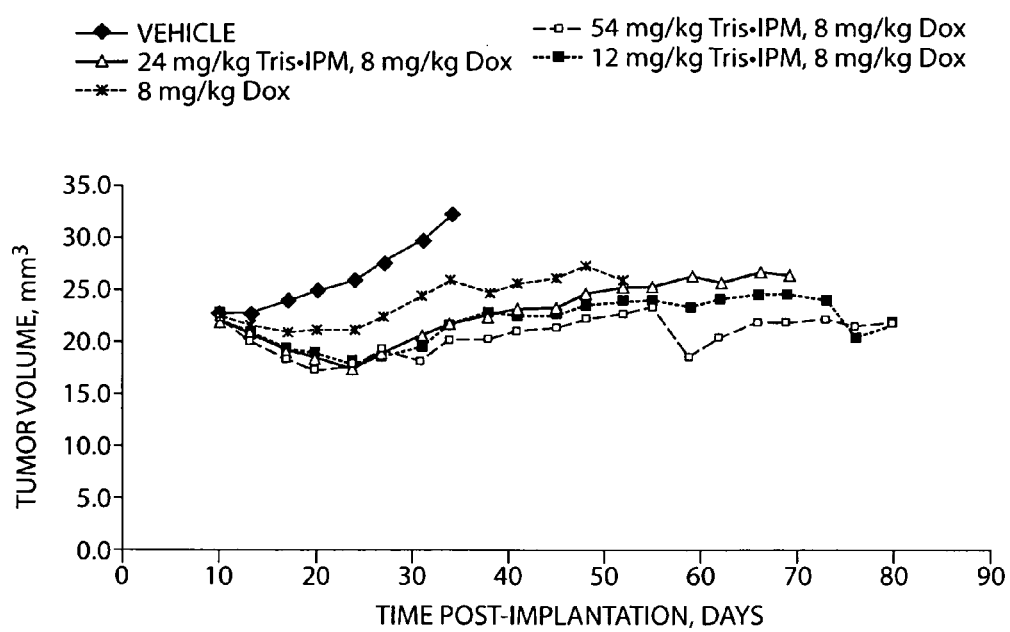
FIG. 25 shows the toxicity of IPM•Tris/doxorubicin combination regimen.

The response of the MX-1 human mammary tumor xenografts to treatment with (1) vehicle—ip and po, (2) ip IPM•Tris, IPM, and IPM•(LYS)$_2$, and (3) po IPM•Tris, IPM, and IPM•(LYS)$_2$ is shown in FIGS. 16, 17, and 18, respectively.

Conclusions

For ip administration of equivalent IPM dosages the antitumor activity of IPM•Tris was comparable to that for both IPM and IPM•(LYS)$_2$ (higher dosage). The lower dosage was inactive against the MX-1 tumor in this study. The highest tolerated dosage of IPM•Tris was superior to the highest tested dosage of either IPM or IPM•(LYS)$_2$. For po administration of equivalent IPM dosages, the antitumor activity of the IPM•Tris was comparable to that for both IPM and IPM•(LYS)$_2$ at the lower dosage. The dosage of 120 mg/kg/dose was toxic to the mice for both IPM•Tris and IPM.

In the previous MX-1 study (Example 7) for ip administration of equivalent IPM dosages the antitumor activity of IPM•Tris was superior to that for IPM (both dosages) and comparable to that for IPM•(LYS)$_2$ (both dosages). For po administration of equivalent IPM dosages, the antitumor activity of IPM•Tris was comparable to that for IPM (both dosages), comparable to that for IPM•(LYS)$_2$ at the higher dosage, and superior to that for IPM•(LYS)$_2$ at the lower dosage.

In comparing the two studies the activity of the three agents when administered ip was less in this study (e.g., for IPM•Tris at a dosage of 36 mg/kg/dose—T-C value of 10.2 days vs. 3.3 days; for IPM at a dosage of 36 mg/kg/dose—T-C value of 5/2 days vs. 1.1 days; and for IPM•(LYS)$_2$ at a dosage of 56 mg/kg/dose—T-C value of 9.0 days vs. 0.3 day). The activity of IPM•Tris when administered po was also less (comparable values for IPM and IPM•(LYS)$_2$) in this study (e.g. for IPM•Tris at a dosage of 81 mg/kg/dose—T-C value of 9.0 days vs. 2.6 days; for IPM at a dosage of 81 mg/kg/dose—T-C value of 4.0 days vs. 2.3 days; and for IPM•(LYS)$_2$ at a dosage of 280 mg/kg/dose—T-C value of 5.0 days vs. 3.9 days). The reason(s) for the decreased activity is not obvious, given the study-to-study variation with such biological systems. With respect to the tumor component of the study, the vehicle-treated control tumors grew at comparable rates in the two studies. The median tumor weights on the first day of treatment were slightly larger in Example 7 (range of 172-197 mg) than in this example (range of 144-162 mg); however, this small difference should have no significant effect on the antitumor activity.

Example 9

Materials and Methods

Three groups of eight mice were treated with IPM•Tris, which may be prepared as described in Example 1, three groups of eight mice were treated with doxorubicin, one group of ten mice was treated with vehicle, and eighteen groups of eight mice were treated with the IPM•Tris/doxorubicin combination. MX-1 tumor fragments (30-40 mg, from an in vivo passage) were implanted subcutaneously in the mammary fat pad in female athymic nude mice. IPM•Tris (or its vehicle) was given intraperitoneally daily for five consecutive days (Q1d×5) at three dosages (12, 24, and 54 mg/kg/dose), wherein the IPM•Tris formulation comprised 258.9 mg IPM (MW 221.02), 141.9 mg Tris base (MW 121.14, molar ratio IPM:Tris base 1:1), and 3% Mannitol. Doxorubicin (or its vehicle) was given intravenously every fourth day for three injections (Q4d×3) at 8 mg/kg/dose). Dosing solutions were prepared on the day of treatment and IPM•Tris dosing solutions were kept on ice once prepared.

Treatment began when tumors were approximately 175 mg in size (range of 100 to 250 mg). Each tumor was measured by caliper in two dimensions and converted to tumor mass using the formula for a prolate ellipsoid (a'b$^2$/2), where a is the longer dimension and b is the smaller dimension, assuming unit density (1 mm$^3$=1 mg). Tumor measurements were recorded twice weekly and antitumor activity was assessed by the delay in tumor growth of the treated groups in comparison to the vehicle-treated control group, partial and complete regressions, and tumor-free survivors. Note that when IPM•Tris was administered at 54 mg/kg/day in combination with doxorubicin at 8 mg/kg/day, two animals in the combination group died early due to toxicity. Results can be seen in FIGS. 19-25.

The combination of IPM•Tris with doxorubicin resulted in significant antitumor activity, where tumor growth inhibition by the combination exceeded that observed with single agent administration and the combination significantly increased survival in comparison to single agent administration. In fact, the effect of the combination shows synergistic efficacy, that is, greater than additive efficacy compared to the agents administered individually in like doses, even where the dosage of IPM•Tris alone is so low as to provide little or no improvement when compared to a vehicle-treated control animal. While animal weights in the combination groups were reduced during treatment (average animal weights reduced by 20% at end of dosing at day 22), they quickly recovered once dosing ended (full recovery was observed by day 38), suggesting that toxicity was reversible. This data suggests that combination therapy with IPM•Tris and doxorubicin may be useful for treating any cancer that responds to either doxorubicin or IPM•Tris as single agents or in combination, including but not limited to, breast cancer, ovarian cancer, and sarcoma.

Example 10

Figure 26:
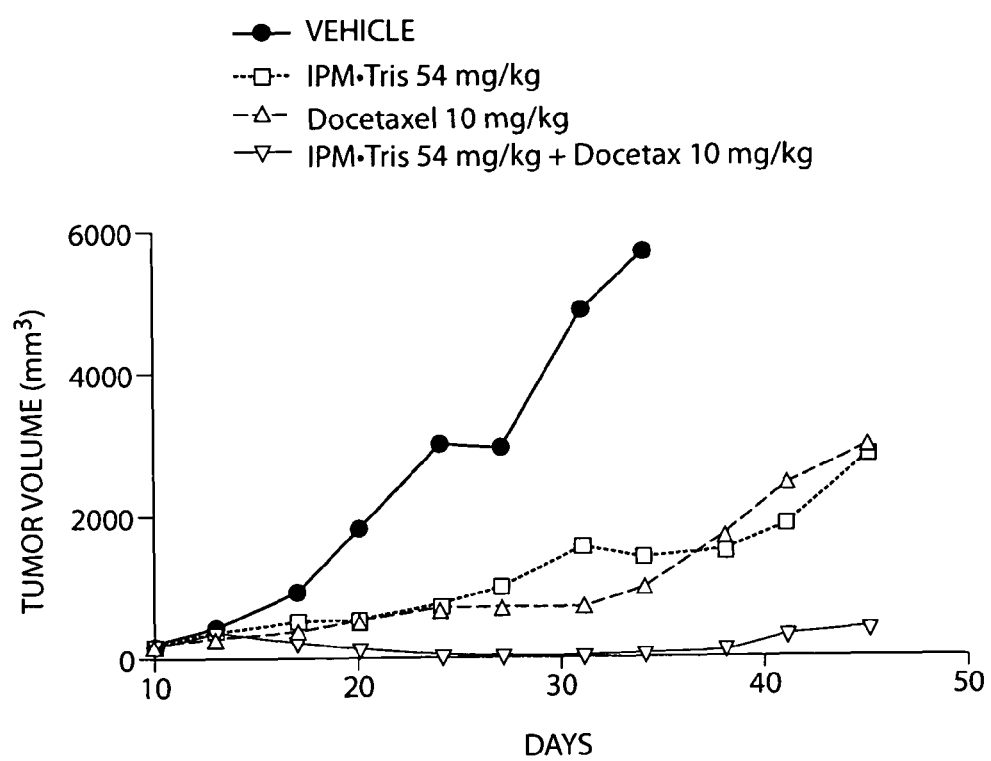
FIG. 26 shows the effect on MX-1 breast cancer tumors of treatment with IPM•Tris in combination with docetaxel with a dose of 54 mg/kg IPM•Tris Q1D×5 IP and 10 mg/kg docetaxel Q6D×3 IV.

Fragments (30 to 40 mg each) of MX-1 human mammary tumors from an in vivo passage were implanted subcutaneously in nude mice in the mammary fat pad and were allowed to reach 75 to 198 mg in weight before initiation of treatment. IPM•Tris (54 mg/kg), which may be prepared as described in Example 1, and docetaxel (10 mg/kg) were administered Q1D×5 IP and Q6D×3 IV, respectively, starting ten days after tumor implantation. The combination of the two agents demonstrated an increased antitumor effect compared to either agent administered as a single agent as seen in FIG. 26.

Example 11

Figure 27:
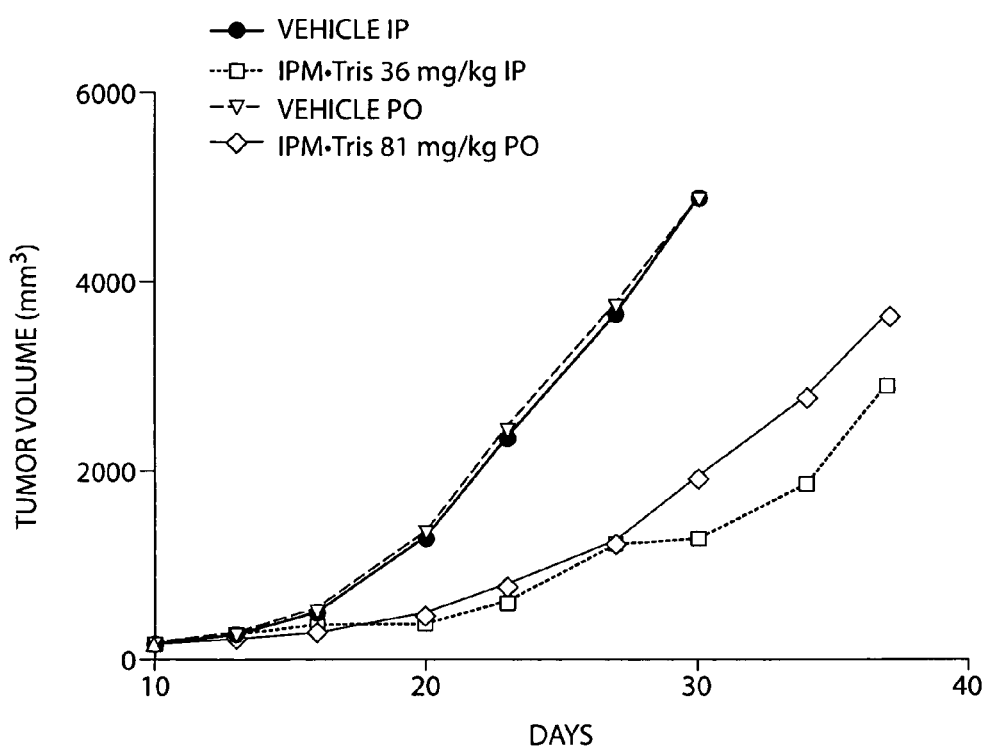
FIG. 27 shows the effect on MX-1 breast cancer tumors of treatment with IPM•Tris administered either at a dose of 36 mg/kg IP or at a dose of 81 mg/kg PO.
Figure 28:
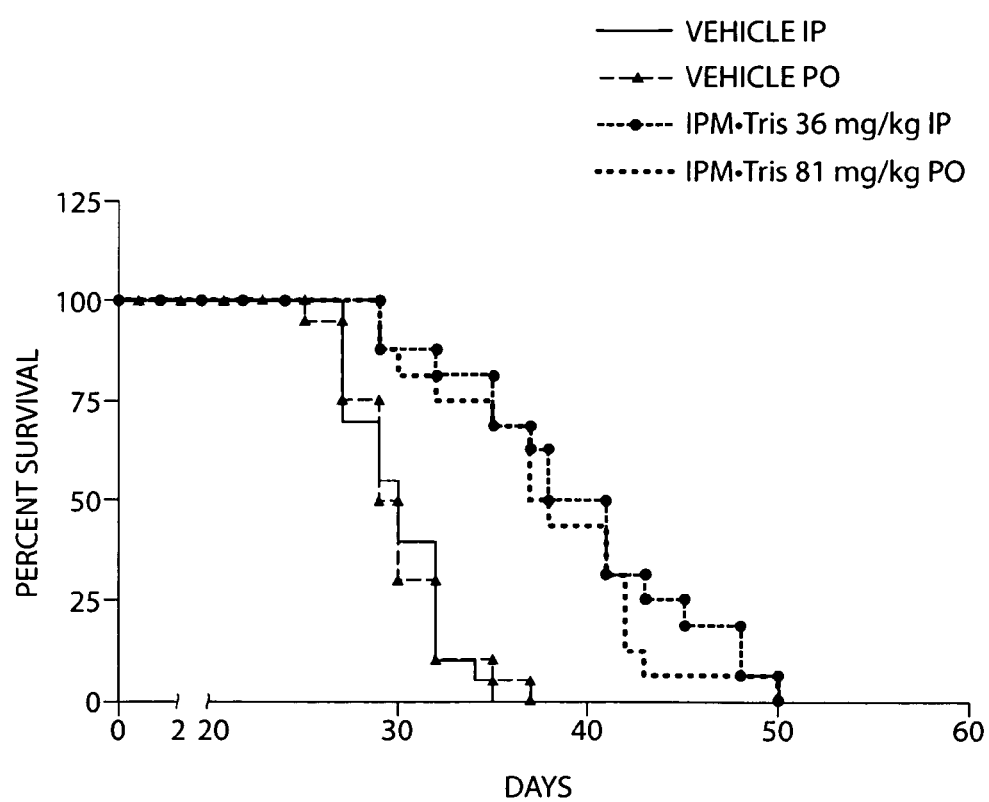
FIG. 28 shows the effect on survival of IPM•Tris administered either at a dose of 36 mg/kg IP or at a dose of 81 mg/kg PO.

Fragments (30 to 40 mg each) of MX-1 human mammary tumors from an in vivo passage were implanted subcutaneously in nude mice in the mammary fat pad and were allowed to reach 75 to 198 mg in weight before the start of treatment. IPM•Tris (36 mg/kg), which may be prepared as described in Example 1, administered IP was found to suppress tumor growth to approximately the same extent as IPM•Tris (81 mg/kg) administered PO as seen in FIG. 27. Additionally, the oral or systemic administration of IPM-Tris resulted in similar increases in survival of MX-1 xenograft-bearing mice. The median survival of the IP group was 39 days, the median survival of the PO group was 37.5 days, and the median survival of the vehicle control group was 30 days as seen in FIG. 28. The equivalent antitumor activity of these PO and IP doses is within the range expected from the PK of orally and systemically administered IPM•Tris.

Example 12

Figure 29:
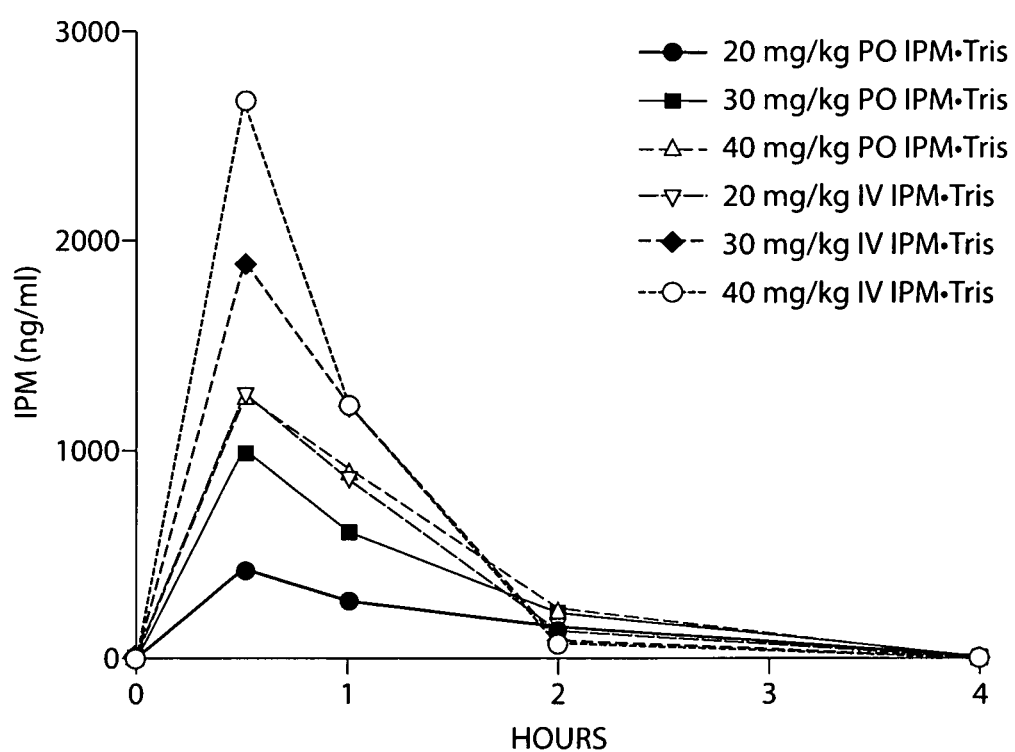
FIG. 29 shows the pharmacokinetics of oral and IV administered IPM•Tris in female Sprague-Dawley rats.
Figure 30:
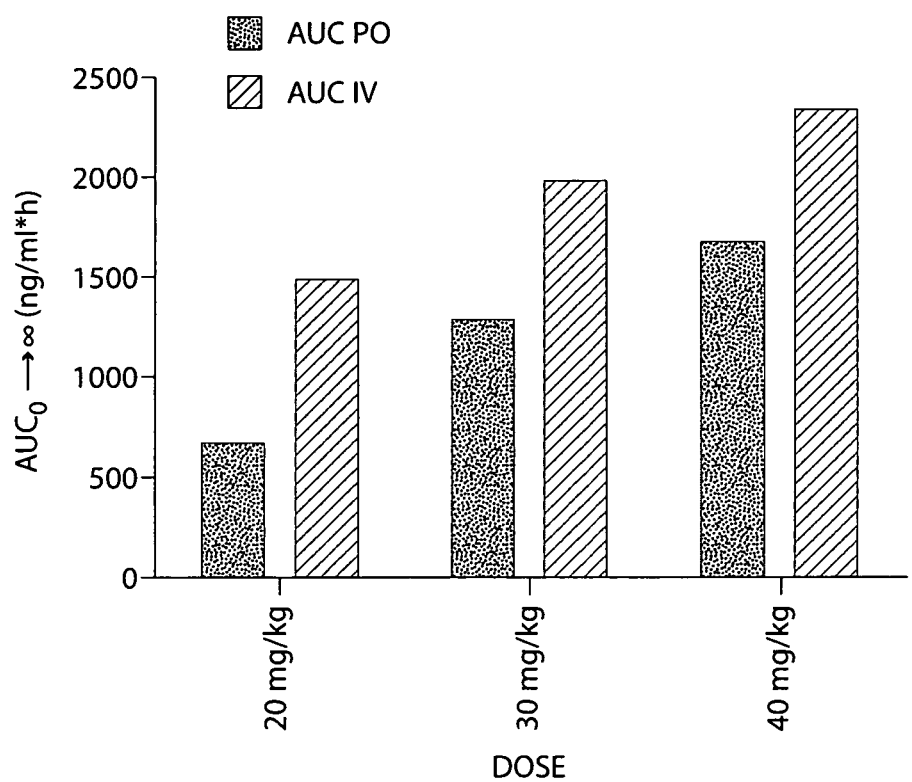
FIG. 30 shows the AUC with increasing doses of PO- or IV-administered IPM•Tris.
Figure 31:
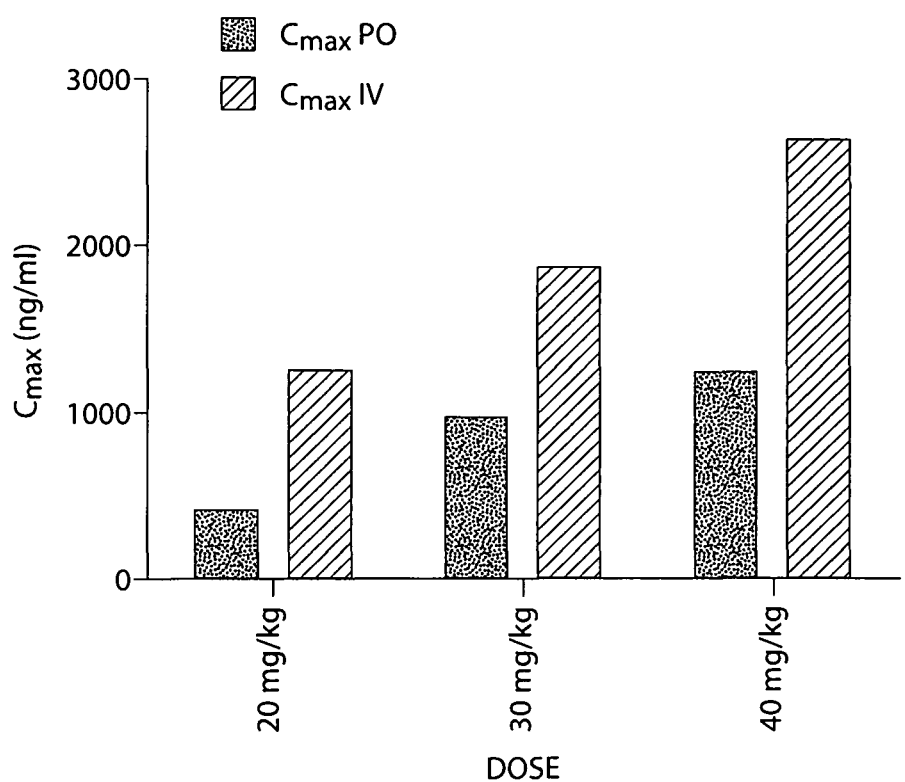
FIG. 31 shows the $C_{max}$ with increasing doses of PO- or IV-administered IPM•Tris.

Sprague-Dawley rats were administered IPM•Tris, which may be prepared as described in Example 1, once daily via gavage (PO) or bolus IV injection. IPM•Tris was administered in doses of 20, 30, or 40 mg/kg and blood samples for PK evaluation were obtained pre-dose and at 0.5, 1, 2, 4, 6, 8, 12, and 24 hours post-dose from the retro orbital sinus. Three animals per group were sampled at each time point. PK results for pre-dose, 0.5, 1, 2, and 4 hours are shown in FIG. 29 where $T_{max}$ appeared to be approximately 0.5 hours. Estimates of terminal $t_{1/2}$ ranged from 0.25 to 0.64 hours. For each dose, AUC values were used to estimate absolute bioequivalence of orally administered IPM•Tris as the ratio (AUC post-PO dose)/(AUC post-IV dose). AUC values for each dose are shown in FIG. 30 and $C_{max}$ values for each dose are shown in FIG. 31. Both AUC and $C_{max}$ values increased linearly with increasing dose of PO- or IV-administered IPM•Tris.

Bioavailability of the 20, 30, and 40 mg/kg PO doses of IPM•Tris were 48%, 65%, and 73%, respectively. Overall mean bioavailability was 62% in females. Similar PK was observed in rats; however, mean bioavailability in males was estimated to be 41%.

Example 13

Solution Stability of IPM•Tris/Mannitol and IPM•(LYS)$_2$

The reconstituted stability of IPM•Tris formulation was evaluated in 5% sodium chloride solution for injection. The concentration of IPM was found to maintain >90% potency for up to 2.0 hours.

The IPM•(LYS)$_2$ formulation was evaluated in 0.9% sodium chloride solution for injection. The concentration of IPM was found to maintain >90% potency for up to 1.0 hour.

Solution Stability of IPM•Tris/Mannitol

Table 1 presents reconstitution stability data for IPM•Tris/mannitol in the presence of 25 mL of 5% sodium chloride solution for injection. Aliquots were taken at target times of ~1 hr, 1.5 hrs, 2.5 hrs, 3.5 hrs, 4.0 hrs, and 5.0 hrs. Samples were analyzed for IPM potency.

TABLE 1

Reconstitution Stability of IPM.Tris/Mannitol in the Presence of 5% Sodium Chloride Solution

| Reconstitution Time (hours) | % Potency based on Original IPM Vial Content |
|---|---|
| 0 | 100 |
| 1 | 94 |
| 2 | 90 |
| 3 | 86 |
| 4 | 81 |
| 6 | 74 |

Solution Stability of IPM•(LYS)$_2$

Table 2 presents reconstitution stability data for IPM•(LYS)$_2$ in the presence of 25 mL of 0.9% sodium chloride solution for injection. Aliquots were taken at target times of ~1 hr, 2 hrs, 2.5 hrs, 3.5 hrs, 4.0 hrs, and 5.0 hrs. Samples were analyzed for IPM•(LYS)$_2$ potency.

TABLE 2

Reconstitution Stability of IPM.(LYS)$_2$ in the Presence of 0.9% Sodium Chloride Solution

| Reconstitution Time (hours) | % Potency based on Original IPM.(LYS)$_2$ Vial Content |
|---|---|
| 0 | 100 |
| 1 | 90 |
| 2 | 79 |
| 2.5 | 71 |
| 3.5 | 64 |
| 4 | 57 |
| 5 | 51 |

Conclusion

IPM/tromethamine/mannitol formulation maintains 90% potency for 2.0 hours when subjected to 5% sodium chloride in solution. IPM•(LYS)$_2$ formulation maintains 90% potency for 1.0 hour in the presence of 0.9% sodium chloride. The difference in the reconstitution stability (>90% potency) between the two formulations is 1.0 hours, a factor of two. The increase in stability time may assist clinicians during preparation and administration of drug product.

Example 14

Solution Stability of IPM

Figure 32:
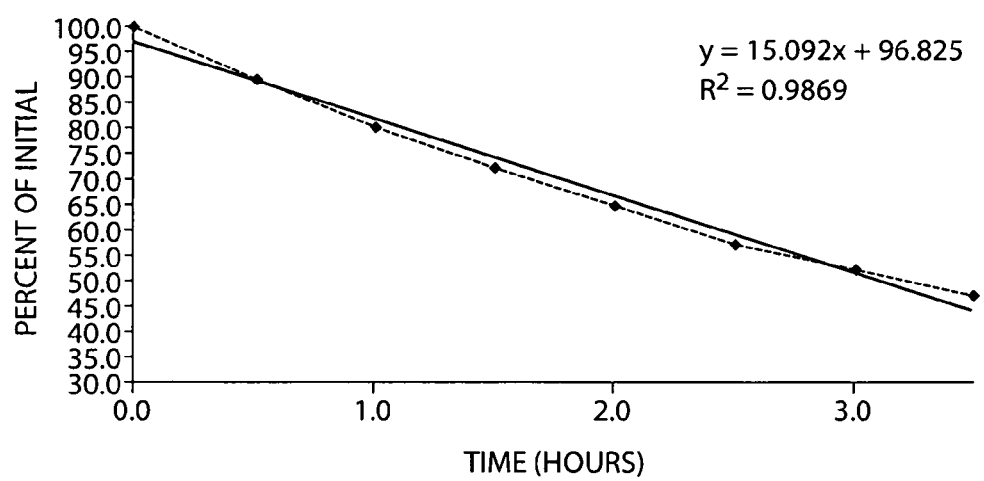
FIG. 32 shows the solution stability of IPM in pH 7.0 buffer at 25° C.

The reconstituted stability of IPM formulation was evaluated in pH 7 buffer at approximately 25° C. over 3.5 hours as shown below in Table 3 and in FIG. 32.

| Reconstitution Time (hours) | % Purity |
|---|---|
| 0 | 100.00% |
| 0.5 | 89.5% |
| 1.0 | 80.3% |
| 1.5 | 72.2% |
| 2.0 | 64.8% |
| 2.5 | 57.4% |
| 3.0 | 52.1% |
| 3.5 | 47.0% |

Solution Stability of IPM•Tris/Mannitol

Table 4 presents reconstitution stability data for IPM·Tris/Mannitol in the presence of 25 mL of 5% sodium chloride solution for injection. Aliquots were taken at target times of 1.5, 3.0, and 4.5 hours.

| Reconstitution Time (hours) | Purity (%) |
|---|---|
| 0 | 99.80 |
| 1.5 | 99.72 |
| 3.0 | 99.49 |
| 4.5 | 99.50 |

Solution Stability of IPM·(LYS)$_2$

Table 5 presents reconstitution stability data for IPM·(LYS)$_2$ in the presence of 25 mL of 0.9% sodium chloride solution for injection. Aliquots were taken at target times of 1.5, 3.0, and 4.5 hours.

| Reconstitution Time (hours) | Purity (%) |
|---|---|
| 0 | 97.48 |
| 1.5 | 96.97 |
| 3.0 | 92.54 |
| 4.5[3] | 95.37 |

Example 15

Stability of Solid IPM•Tris

| | | One month | Two months | Three months |
|---|---|---|---|---|
| Purity (% area) | −20° C. | 100.0% | 100.0% | 100.0% |
| | 5° C. | 99.9% | 100.0 | 100.0% |
| | 25° C. | 100.0% | 99.8% | 99.9% |
| Potency (IPM content % w/w) | −20° C. | 100.5% | 100.4% | 102.4% |
| | 5° C. | 101.3% | 99.6% | 102.3% |
| | 25° C. | 97.8% | 90.9% | 80.8% |

Stability of Solid IPM•Tris/Mannitol Lyophilisate

| | | Time zero | 1 month | 3 months | 6 months | 9 months |
|---|---|---|---|---|---|---|
| Purity (% area) | −70° C. | 98.5% | 98.7% | 98.7% | 99.7% | 99.8% |
| | −20° C. | 98.5% | 98.6% | 99.1% | 99.3% | 99.8% |
| | 5° C. | 98.5% | 99.1% | 98.9% | 99.2% | 99.8% |

Stability of Solid IPM•(LYS)$_2$ Lyophilisate

| | | Time zero | 1 month | 3 months | 6 months | 9 months | 12 months | 18 months | 24 months |
|---|---|---|---|---|---|---|---|---|---|
| Purity (% area) | −70° C. | 99.8% | 98.8% | 98.8% | 99.5% | 99.8% | 99.6% | 100.0% | 100.0% |
| | −20° C. | 99.8% | 98.4% | 98.5% | 96.0% | 96.9% | 97.1% | | |
| | 5° C. | 99.8% | 93.1% | 54.8% | 49.2% | | | | |

Example 16

| Condition | IPM Free acid (API) | IPM-Tris salt (API) | IPM-Lysine Injectable | IPM-Tris-Mannitol Injectable |
|---|---|---|---|---|
| Current Stability Data Summary | No change in purity at | No change in purity at | No change in purity at | No change in purity at |

| Condition | IPM Free acid (API) | IPM-Tris salt (API) | IPM-Lysine Injectable | IPM-Tris-Mannitol Injectable |
|---|---|---|---|---|
| Long-Term Storage Temperature | −70° C., 2 years −70° C. | 5° C., 3 mo. 5° C. | −70° C., 2 years −70° C. | 5° C., 1 year 5° C. |
| Solubility at 25° C. (saline) | 14 mg/ml | ~1400 mg/ml | 20 mg/ml | 80 mg/ml1 |
| Reconstitution Solubility Time | NA | NA | <40 seconds | <30 seconds |
| Reconstitution Stability at 25° C. | NA | NA | 45 minutes | 2.5 hours |
| Stability in 250 ml 0.9% saline | NA | NA | >90% potency for 15 min | >90% potency for 45 min |
| pH | 3.02 | NA | 8.5 | 5.0 |

Equivalents

Those skilled in the art will recognize, or be able to ascertain using no more than routine experimentation, numerous equivalents to the compounds and methods of use thereof described herein. Such equivalents are considered to be within the scope of this invention and are covered by the following claims.

All of the above-cited references and publications are hereby incorporated by reference.

We claim:

1. A crystalline compound comprising IPM or an analog thereof, having a structure of formula (I)

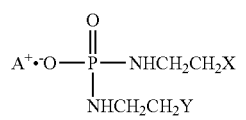

wherein A$^+$ is the conjugate acid of a hydroxylated aliphatic amine; and
X and Y independently represent leaving groups,
wherein the melting point of the crystalline compound is about 103 to about 106° C.

2. A crystalline compound of claim 1, wherein A$^+$ is selected from the conjugate acid of mono-, bis- or tris-(2-hydroxyethyl)amine, 2-hydroxy-tert-butylamine, N,N-dimethyl-N-(2-hydroxyethyl)amine, and tris(hydroxymethyl)aminomethane (Tris).

3. A crystalline compound of claim 2, wherein A$^+$ is conjugate acid of Tris.

4. A crystalline compound of claim 1, wherein X and Y are independently halogen.

5. A crystalline compound of claim 4, wherein X and Y are the same.

6. A crystalline compound of claim 5, wherein X and Y are both Cl.

7. A crystalline compound of claim 1, wherein the IPM or analog thereof and the ammonium species are present in a ratio from 2:1 to 1:2.

8. A crystalline compound of claim 7, wherein the IPM or analog thereof and the ammonium species are present in a ratio of 1:1.

9. A crystalline compound of claim 1, wherein the melting point of the crystalline compound is 105 to 106° C.

10. A crystalline compound of claim 1, wherein the crystalline compound comprises a single polymorphic form of crystals.

11. A crystalline compound of claim 1, wherein the compound is stable at room temperature in the presence of water for at least one day.

12. A crystalline compound of claim 11, wherein the compound is stable at room temperature in the presence of water for at least three days.

13. A crystalline compound of claim 12, wherein the compound is stable at room temperature in the presence of water for at least six days.

14. A method for preparing a pharmaceutical composition, comprising dissolving a crystalline compound of claim 1 in a saline solution.

15. A method of claim 14, wherein the solution is stable at room temperature for at least about 120 minutes.

16. A method of claim 14 or 15, wherein the pharmaceutical composition is formulated adapted for oral, topical, transdermal, or parenteral administration.

17. A method of claim 16, wherein the pharmaceutical composition is formulated for parenteral administration.

18. A pharmaceutical composition adapted for oral administration, comprising a pharmaceutically acceptable diluent or excipient and a crystalline compound of the formula

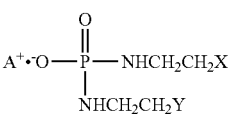

wherein A$^+$ represents an ammonium species selected from the protonated (conjugate acid) or quaternary forms of aliphatic amines and aromatic amines, including basic amino acids, heterocyclic amines, substituted and unsubstituted pyridines, guanidines and amidines; and
X and Y independently represent leaving groups,
wherein the melting point of the crystalline compound is about 103 to about 106° C.

19. A method of claim 16, wherein the pharmaceutical composition is formulated adapted for oral administration.

20. A composition comprising the crystalline compound of claim 1 and one or more of a microtubule binding agent, DNA intercalator or cross-linker, DNA synthesis inhibitor, DNA and/or RNA transcription inhibitor, antibody, enzyme, enzyme inhibitor, gene regulator, and/or angiogenesis inhibitor.

21. The composition of claim 20, wherein the composition comprises an enzyme inhibitor.

22. The composition of claim 21, wherein the enzyme inhibitor is etoposide.

23. The composition of claim 20, wherein the composition comprises a DNA intercalator or cross-linker.

24. The composition of claim 23, wherein the DNA intercalator or cross-linker is carboplatin.

25. The composition of claim 18, further comprising one or more of a microtubule binding agent, DNA intercalator or cross-linker, DNA synthesis inhibitor, DNA and/or RNA transcription inhibitor, antibody, enzyme, enzyme inhibitor, gene regulator, and/or angiogenesis inhibitor.

26. The composition of claim 25, wherein the composition comprises an enzyme inhibitor.

27. The composition of claim 26, wherein the enzyme inhibitor is etoposide.

28. The composition of claim 25, wherein the composition comprises a DNA intercalator or cross-linker.

29. The composition of claim 28, wherein the DNA intercalator or cross-linker is carboplatin.

* * * * *

UNITED STATES PATENT AND TRADEMARK OFFICE
CERTIFICATE OF CORRECTION

PATENT NO. : 8,604,007 B2 Page 1 of 1
APPLICATION NO. : 12/080812
DATED : December 10, 2013
INVENTOR(S) : John C. Amedio JR.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1496 days.

Signed and Sealed this
Twenty-third Day of May, 2017

Michelle K. Lee
*Director of the United States Patent and Trademark Office*